United States Patent [19]
Suzuki et al.

[11] Patent Number: 5,822,063
[45] Date of Patent: Oct. 13, 1998

[54] APPARATUS FOR MEASURING MAGNETO-OPTICAL EFFECT

[75] Inventors: Takao Suzuki; William Van Drent, both of Nagoya, Japan

[73] Assignee: Toyota Jidosha Kabushiki Kaisha, Aichi, Japan

[21] Appl. No.: 840,907

[22] Filed: Apr. 17, 1997

[30] Foreign Application Priority Data

Apr. 18, 1996 [JP] Japan ................................ 8-096887

[51] Int. Cl.$^6$ ...................................................... G01J 4/00
[52] U.S. Cl. ........................................... 356/364; 356/369
[58] Field of Search .................................. 356/364, 369, 356/51, 365–368

[56] References Cited

U.S. PATENT DOCUMENTS 5,278,630  1/1994  Maruyama ............................. 356/328

FOREIGN PATENT DOCUMENTS 63-122930 A  5/1988  Japan .
534277A  2/1993  Japan .

OTHER PUBLICATIONS

Magnetooptical Kerr Spectrometer for 1.2–5.9 eV Region and its Application to FePt/Pt Multilayers, Jpn. J. Appl. Phys., vol. 32 (1993), pp. 989–995.

Primary Examiner—Frank G. Font
Assistant Examiner—Amanda Merlino
Attorney, Agent, or Firm—Kenyon & Kenyon

[57] ABSTRACT

An apparatus for measuring magneto-optical effect includes a light source 102, a spectroscope 120, a first polarizer 150 to polarize the light with a required wavelength taken out by the spectroscope 120, means 172 for applying magnetic field on a sample 176, a second polarizer 156 to admit the light transmitted or reflected by a sample 176 to pass, a photo-detector 162 for detecting intensity of light that has passed the second polarizer 156. The light source 102 includes a heavy hydrogen lamp and the spectroscope does not contain a lens and/or prism. A light path from the light source to the photo-detector is housed in a container, and the container is filled with a gas containing no oxygen.

20 Claims, 21 Drawing Sheets

APPARATUS FOR MEASURING MAGNETO-OPTICAL EFFECT

BACKGROUND OF THE INVENTION

1. Field of the Invention

The present invention relates to technology for measuring magneto-optical Faraday effect and/or Kerr effect.

2. Description of the Prior Art

The latest apparatus for measuring magneto-optical effects is disclosed in Jpn. J. Appl. Phys. Vol. 32 (1993) pp. 989–995. In this apparatus, light from a light source is fed into a spectroscope from which light with a required wavelength is taken out. After being turned into linearly polarized light by a first polarizer, the light thus taken out is irradiated on a sample to which a magnetic field is applied. Intensity of light which has passed through the sample is detected to measure the magneto-optical Faraday effect. Intensity of light which is reflected by the sample is detected to measure the magneto-optical Kerr effect. In either case, intensity of the light transmitted or reflected by the sample is detected after the light has passed through a second polarizer. This measuring concept is common to methods of crossed-Nicols, Faraday-cell, rotational analyzer method and circularly polarized light modulation method for measuring magneto-optical effects.

In ultra-high-density memory technology utilizing magneto-optical effect, wavelength of light to be used for writing and reading is becoming shorter and shorter in order to increase density of memory. It is now desired to utilize technology for measuring magneto-optical effects by the light with ultra-short wavelength.

The apparatus disclosed in the above mentioned magazine is so improved as to be able to measure the magneto-optical effects by light with wavelength down to some 210 nm. However, this apparatus is not suitable for measurement by light with wavelength shorter than 200 nm, since a xenon lamp is used as a light source. Intensity of light from the xenon lamp is very weak in a wavelength range below 200 nm. As long as a xenon lamp is used as a light source, measurement by light with wavelength shorter than 200 nm is impractical. In order to make the measurement practical with wavelength shorter than 200 nm, one may think of adopting a heavy hydrogen lamp as a light source. However, no apparatus with a heavy hydrogen lamp as a light source has been realized yet.

While wavelength of light emitted by the heavy hydrogen lamp extends down to below 200 nm, intensity of light with wavelengths below 200 nm is so weak that it is extremely difficult to obtain a required signal to noise (S/N) ratio and reliable measurement. Another problem is that light with wavelengths shorter than 200 nm is quickly absorbed by the air or lens which also makes the measurement with the short wavelength difficult. In other words, the use of the heavy hydrogen lamp does not automatically make it possible to make measurements with wavelength shorter than 200 nm. A number of obstacles have to be overcome to obtain the required S/N ratio.

SUMMARY OF THE INVENTION

One of the objects of the invention is to realize an apparatus for measuring magneto-optical effects by light with wavelength shorter than 200 nm.

The other object of the invention is to realize an apparatus in which absorption of light is effectively prevented to realize S/N ratio required for a reliable measurement.

The apparatus of the invention comprises a light source, a spectroscope to separate light from the light source into a spectral component with required wavelength, a first polarizer to polarize the separated light spectrum with the required wavelength, means for applying a magnetic field to a sample, a second polarizer to polarize light transmitted or reflected by the sample and a detector to detect intensity of light which has passed through the second polarizer. Here, a heavy hydrogen lamp is used as the light source, a spectroscope containing no lens and/or prism is used, a light path from the light source to the detector is enclosed in a container and the air inside the container is replaced with gas containing no oxygen.

Since the spectroscope of the present invention does not have such optical components as lens and prism for quickly absorbing light with short wavelength, the light spectrum with the wavelength shorter than 200 nm is not absorbed very much in the spectroscope. Furthermore, since the light path is enclosed in the gas containing no oxygen, light with short wavelength is not absorbed very much by oxygen. The inventors had thought that light with wavelengths shorter than 200 nm were not transmitted well in a medium other than in vacuum. The light with wavelengths shorter than 200 nm is often called vacuum ultraviolet ray. Contrary to the expectation, however, the inventors found that light with short wavelengths is well transmitted without serious attenuation in a gas when oxygen is removed from the gas. It is not necessary to enclose the light pass in vacuum. Instead, the container for enclosing the light pass can be filled with the gas. This makes the design of the apparatus greatly simplified.

The apparatus of the present invention is preferably provided with means to modulate, in a specified frequency, the light to be irradiated on the sample and means to measure intensities of a direct current component, a modulation frequency component and a component of a frequency twice as high as the modulation frequency from the values detected by the detector. This apparatus allows simultaneous measurements of an angle of rotation and an ellicipticity of magneto-optical effect, using circularly polarized light modulation method.

It is desired that a second lamp that has a wavelength range in a zone of longer wavelength than those of the heavy hydrogen lamp is provided with the apparatus. In this case, means for selectively inputting light from one of these two lamps into the spectroscope is required. With this apparatus alone, it is possible to make measurements over a wide range of wavelengths from shorter to longer wavelength zones.

It is also preferable that the light condensing system of the apparatus consists of mirrors without including lenses. In this apparatus, light with short wavelength is not attenuated in the condensing system and the required S/N ratio can be secured.

The foregoing and other objects, features, aspects and advantages of the present invention will become more apparent from the following detailed description of the present invention when taken in conjunction with the accompanying drawings.

DETAILED DESCRIPTION OF THE PREFERRED EMBODIMENT

Figure 1:
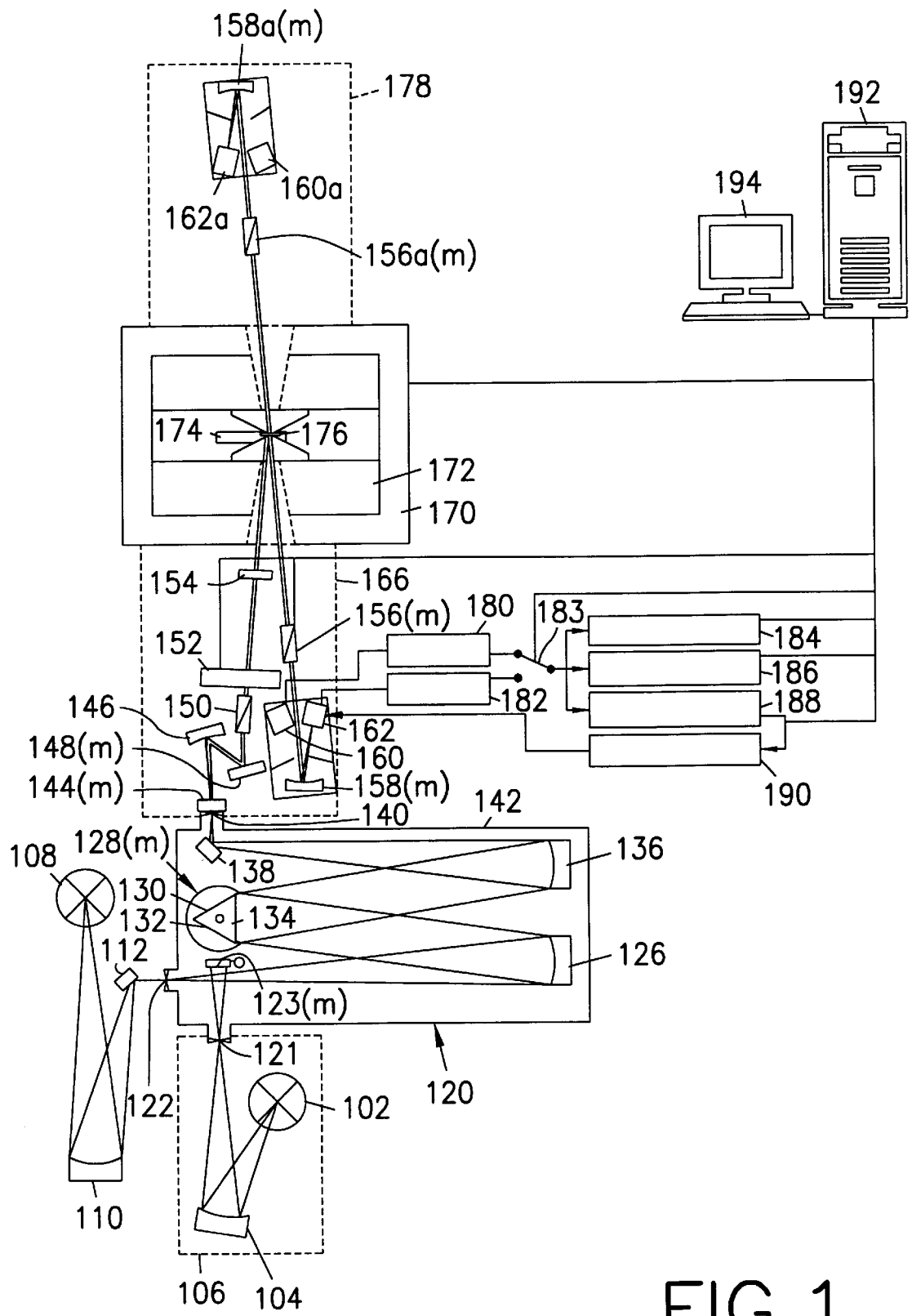
FIG. 1 is a plan view of a layout of an apparatus for the measurement of magneto-optical effects according to an embodiment of the present invention.

An embodiment of the invention will now be described with reference to the accompanying drawings. FIG. 1 is a plan view of an overall layout of an apparatus for measurement of magneto-optical effects according to an embodiment of the present invention.

In the figure, reference numeral 102 designates a heavy hydrogen lamp which emits light with wavelengths shorter than 200 nm. The emitted light with short wavelength is reflected and condensed by a concave reflecting mirror 104 and is inputted into a spectroscope 120 through a first input slit 121. The concave reflecting mirror 104 is made of quartz (instead of which SiC may be used). A surface of the quartz is polished and coated with Pt (instead of which Au may be used) and top-coated with Al—MgF$_2$ so that the reflecting efficiency by the mirror 104 is highest at wavelength of 160 nm. The reflecting efficiency at 160 nm wavelength is 84 to 86 percent. Surfaces of other reflecting mirrors and concave reflectors which will be described later are treated in the same way, so that light with short wavelength is reflected at high rate. The heavy hydrogen lamp 102, the concave reflecting mirror 104 and the first input slit 121 are all enclosed in a container 106 which is filled with nitrogen at atmospheric pressure. The light path from the heavy hydrogen lamp 102 to the first input slit 121 is secured in the oxygen-free atmosphere, so that the light with wavelengths shorter than 200 nm from the heavy hydrogen lamp reaches the spectroscope 120 without significant attenuation. A very small quantity of nitrogen is kept flowing into the container 106, and there is no need to make the container 106 highly airtight. The container 106 does not have to be decompressed, and can be of simple construction.

A xenon lamp 108 is provided with the apparatus from which light with wavelengths longer than that from the heavy hydrogen lamp 102 is emitted. The wavelength range of the xenon lamp 108 overlaps partly with that of the heavy hydrogen lamp 102. For the measurement by light with wavelength shorter than 300 nm, the heavy hydrogen lamp 102 is selected. For the measurement by light with wavelength longer than 300 nm, the xenon lamp 108 is used. Since light with wavelengths longer than 300 nm is hardly absorbed by oxygen, the xenon lamp 108 is placed in the atmosphere. The light from the xenon lamp 108 is reflected and condensed by a concave reflecting mirror 110 and a reflecting mirror 112, and is inputted into the spectroscope 120 through a second slit 122 of the spectroscope 120.

The spectroscope 120 is provided with a selector mirror 123. The selector mirror 123 is arranged near the first input slit 121 and the second input slit 122. Light from either of the input slits 121 and 122 is led into a concave reflecting mirror 126. Marked by the symbol (m) in the figure indicates components movable by step motor (m). For example, the selector mirror 123 can be moved by a step motor 123m. Each step motor is controlled by a computer 192. The selector mirror 123 can be manually switched over by a handle 123a (see FIG. 2).

Figure 2:
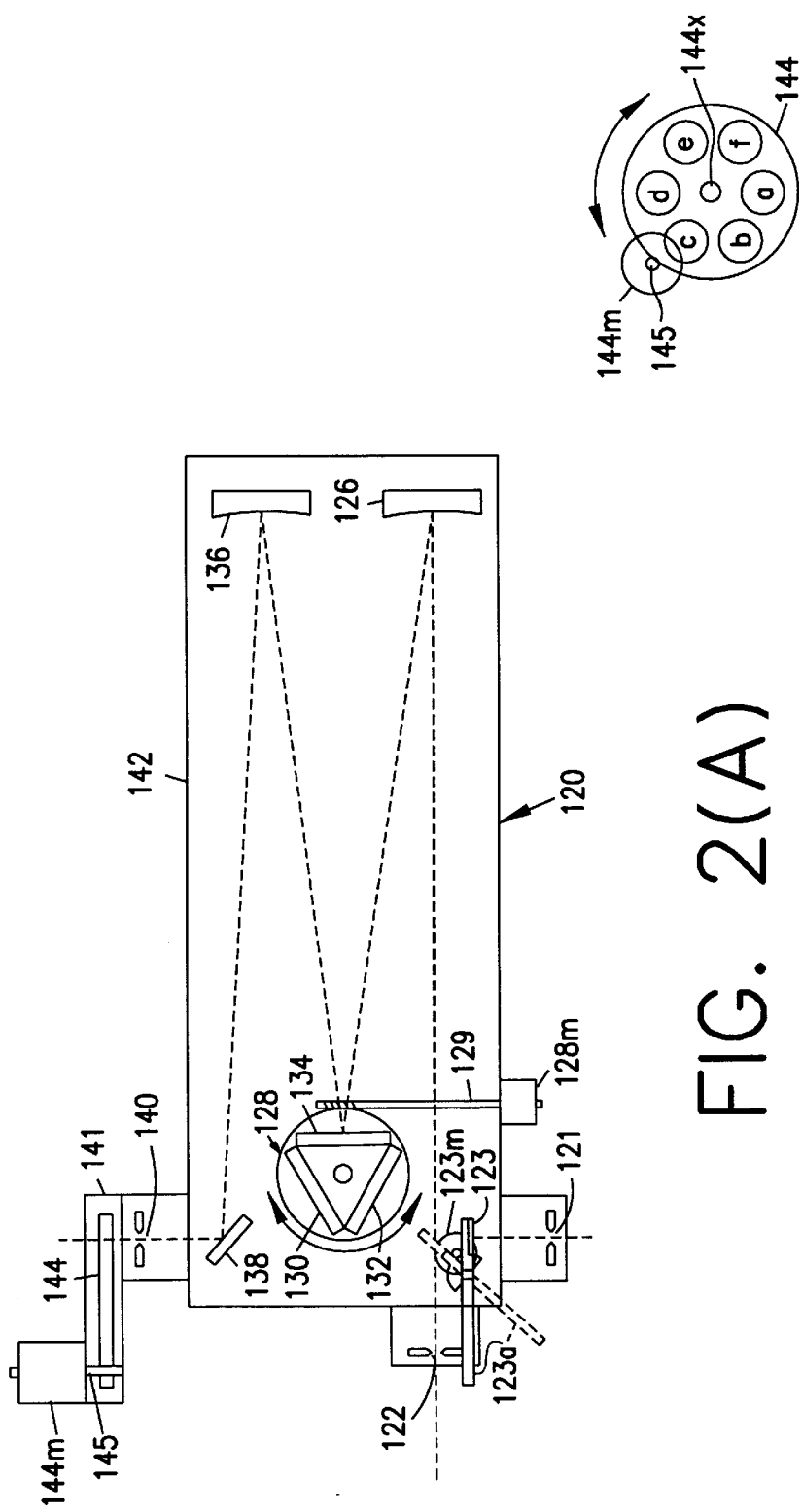
FIGS. 2(A) and 2(B) are a detailed views of a spectroscope and a filter wheel respectively.

As clearly illustrated in FIG. 2, the whole of the spectroscope 120 is placed inside a case 142 filled with nitrogen at atmospheric pressure. The light from either the input slit 121 or the second input slit 122 is reflected by the selector mirror 123 and the concave reflecting mirror 126 before being led into one of diffraction gratings 130, 132 and 134. The three diffraction gratings 130, 132 and 134 are so mounted on a rotary base 128 as to form a triangle in a plan view. The rotary base 128 rotates in a direction of the arrow shown in the figure so that one of the three diffraction gratings can be selected. FIG. 2 shows the diffraction grating 134 in an active position. The rotary base 128 is rotated by a step motor 128m and a warm gear 129. The diffraction grating 130, which has the narrowest grating space, is used for the separation of light with wavelengths shorter than 400 nm. The diffraction grating 134, which has the longest grating space, is designed for diffraction of light with wavelengths longer than 800 nm. The diffraction grating 132, which has intermediate grating space, is used for separation of light with wavelengths between 400 and 800 nm.

The step motor 128m works to select one of the diffraction gratings 130, 132 and 134 and also to fine adjust a rotational angle of the selected diffraction grating so as to select wavelength of light reflected toward a concave reflecting mirror 136. A separated light with the required wavelength for measurement by fine adjusting the rotational angle of one of the diffraction gratings is reflected by the concave reflecting mirror 136 and a reflecting mirror 138 so as to be inputted into an output slit 140 of the spectroscope 120. In this way, the light having the required wavelength for measurement is taken out from the spectroscope 120.

Immediately after the output slit 140, a filter 144 is provided to eliminate light having a higher order of diffraction which is reflected by the selected diffraction grating toward the output slit 140. As shown in FIG. 2(B), the filter 144 has a disk which rotates around an axis 144x and which has six through holes. Five of the six through holes are provided with filter plates 144b to 144f. Each filter plate cuts out specific wavelengths. The cut out wavelengths by the filter plates 144b to 144f are different from one another and one of the filter plates is selected in accordance with the wavelength to be used in the measurement. No filter plate is mounted on the through hole 144a through which the light passes unhindered. A selection of the through hole 144a and the filter plates 144b to 144f is carried out by rotating the disk 144 around the rotational axis 144x by a motor 144m.

As shown in FIG. 1, the selected light having the required wavelength for measurement is condensed and irradiated on a surface of a sample 176 by a concave reflecting mirror 146 and a reflecting mirror 148. The concave reflecting mirror 146 condenses the light at the surface of the sample 176. The reflecting mirror 148 can rotate around a horizontal axis and a vertical axis, and the angle thereof is so adjusted that the reflected light by the sample 176 is led to a concave reflecting mirror 158 which will be described later. For this purpose, the reflecting mirror 148 is provided with a horizontal motor 148m1 and a vertical motor 148m2.

Figure 3:
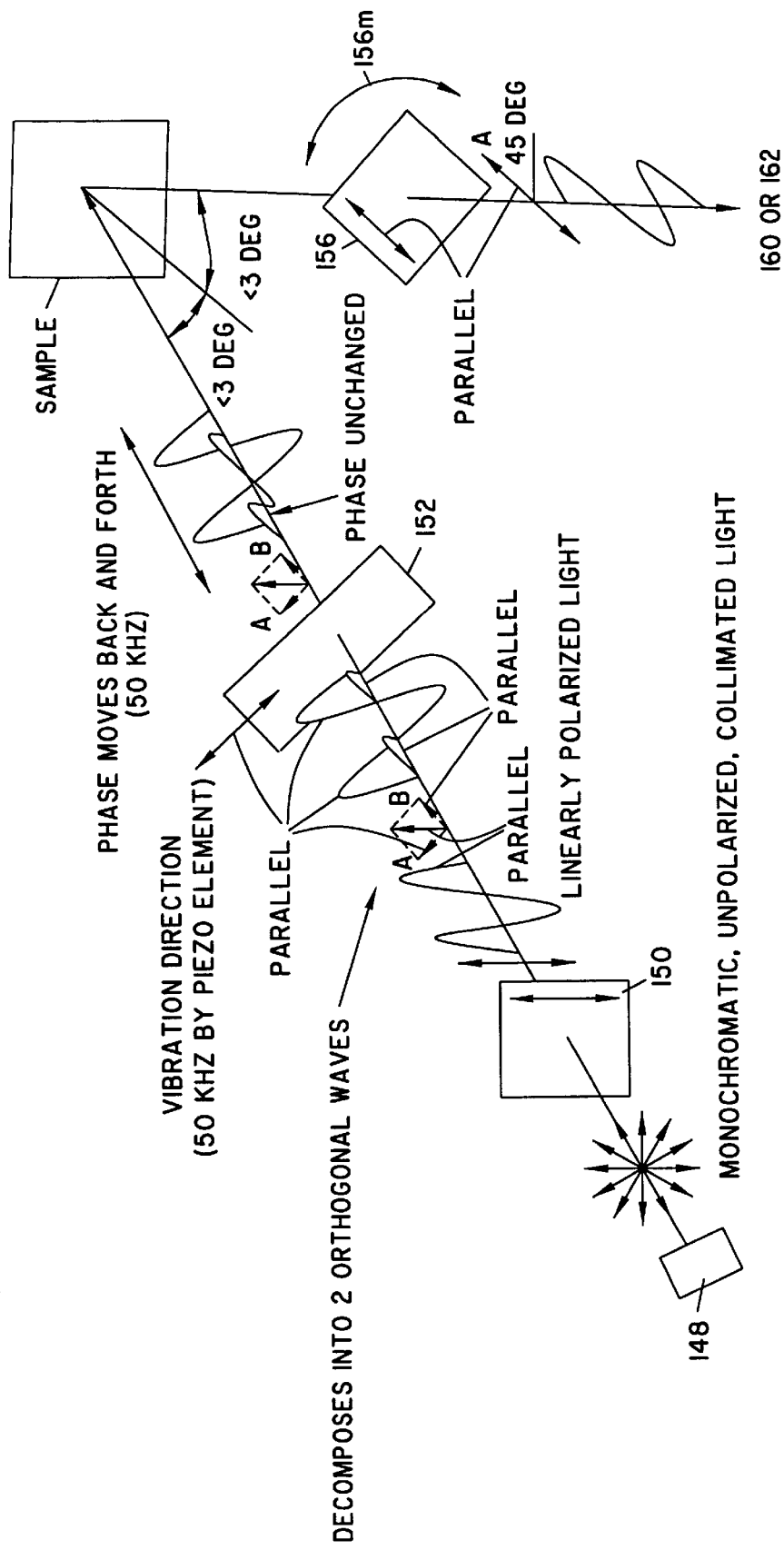
FIG. 3 illustrates principle of measurement.

The reference number 150 in the figure indicates a polarizer, which, as shown in FIG. 3, renders the light linearly polarized as it passes the same. The linearly polarized light passes through a photo-elastic modulator 152. The photo-elastic modulator 152 has a piezo element which vibrates at a frequency of 50 KHz, the vibration direction being tilted 45 degrees in a counter-clock direction with respect to the linearly polarized light.

As shown in FIG. 3, it is understood that the linearly polarized light is composed of wave within a plane tilted 45 degrees in a clockwise direction (indicated in white in the figure) and wave within the plane tilted 45 degrees in the counter-clockwise direction (indicated in black in the figure). The photo-elastic modulator 152 changes phase of the wave in the direction of vibration (black wave) and does not change phase of the wave in the direction perpendicular thereto (white wave). Here, in phase change, the phase gains or retards in a frequency equivalent to the frequency of vibration (50 KHz). That is, as it passes through the photo-elastic modulator 152, the light is modulated into circularly polarized light, the modulation frequency being 50 KHz in this case.

The light which is turned into circularly polarized light in frequency of 50 KHz by the first polarizer 150 and the photo-elastic modulator 152 is irradiated on the sample 176 through an iris 154.

The sample 176 is placed in a sample holder 174 which is provided with light windows formed by a material (fused quartz) that does not absorb light with short wavelengths. The sample holder 174 has a cooler for cooling the sample 176 through adiabatic expansion of liquid nitrogen and a heater for heating the sample 176. The cooler and heater unit makes it possible to change the temperature of the sample 176 within a range between −190° C. and 330° C. In addition, the sample holder 174 is filled with an inert gas which keeps the sample from oxidizing in heating. Furthermore, the sample holder 174 is placed in a holed electromagnet 172 which can apply on the sample 176 a magnetic field of up to 20 KOe. The sample 176 and the electromagnet 172 are both housed in a container 170 which is filled with nitrogen gas at atmospheric pressure and is free from oxygen.

An apparatus of such an arrangement is suitable for measurements of either magneto-optical Faraday effect or Kerr effect. For measurement of Faraday effect, a detector is placed in such a position as to detect the light that has passed through the sample 176 (in FIG. 1, the arrangement is indicated by index a). The detector is made up of a second polarizer 156, a concave reflecting mirror 158, a photo-multiplier 162 and a germanium diode 160. The devices for the detector are enclosed in a enclosure 178. The enclosure 178 is also filled with nitrogen gas at atmospheric pressure and is free from oxygen. The second polarizer 156 can rotate in-plane by a step motor 156m, and, as described later, is adjusted to an angle of zero after being rotated during calibration. The photo-multiplier 162 works for detection of light with short wavelengths, while the germanium diode 160 is used to detect light with long wavelengths. The concave reflecting mirror 158, which is rotated by a step motor 158m, condenses light on either the photo-multiplier 162 or the germanium diode 160.

To observe the magneto-optical Kerr effect, the detection devices 156, 158, 160 and 162 are so positioned as to measure the reflected light from the sample 176. In this case, the optical system for incident light and reflected light is all housed in a container 166. Measurements are taken under oxygen-free condition in the container 166. To ensure that the container 166 is free from oxygen, nitrogen is continuously blown in.

The above described motors and photo-elastic modulator are controlled by the computer 192. Measured data are also processed by the computer 192. The reference number 182 in FIG. 1 indicates an amplifier for the photo-multiplier 162 and the number 180 designates an amplifier for the germanium diode 160. The number 183 in the figure is a switch which can be changed over in association with the concave reflecting mirror 158. When the concave reflecting mirror 158 condenses the light on the germanium diode 160, the signal of the amplifier 180 for the germanium diode 160 is inputted into the computer 192. When the light is condensed on the photo-multiplier 162, the signal of the amplifier 182 for the photo-multiplier 162 is inputted into the computer 192.

The reference number 188 in the figure indicates a direct current component voltmeter to detect the direct current component of the detected light intensities, the reference number 186 indicates a first lock-in amplifier to detect the intensity of the component of the modulation frequency (in this case, 50 KHz), and the reference number 184 designates a second lock-in amplifier to detect the intensity of the component of a frequency twice as high (100 KHz) of the modulation frequency. The respective output values from the devices 184, 186 and 188 are inputted to the computer 192 for processing, and the processed results are shown on a display 194.

It will be noted that while the photo-multiplier 162 is at work, voltage applied to the photo-multiplier 162 to adjust gain of the photo-multiplier 162 is feedback controlled based on a direct current component detected by the direct current component voltmeter 188 so that the value detected by the direct current component voltmeter 188 is kept substantially at a constant level.

In measuring the magneto-optical Kerr effect by this apparatus, the angle formed by the incident light and the normal line of the sample is not larger than 3 degrees as illustrated in FIG. 3. The case is the same with the reflected light. When the angle is smaller than 3 degrees, then the precision in measuring the magneto-optical Kerr effect is kept high. The second polarizer 156, as shown in FIG. 3, is used on a basis of an angle at which the polarized light by the photo-elastic modulator 152 passes through the second polarizer 156 and the unpolarized light by the photo-elastic modulator 152 does not pass through the second polarizer (an angle of zero).

Figure 4A:
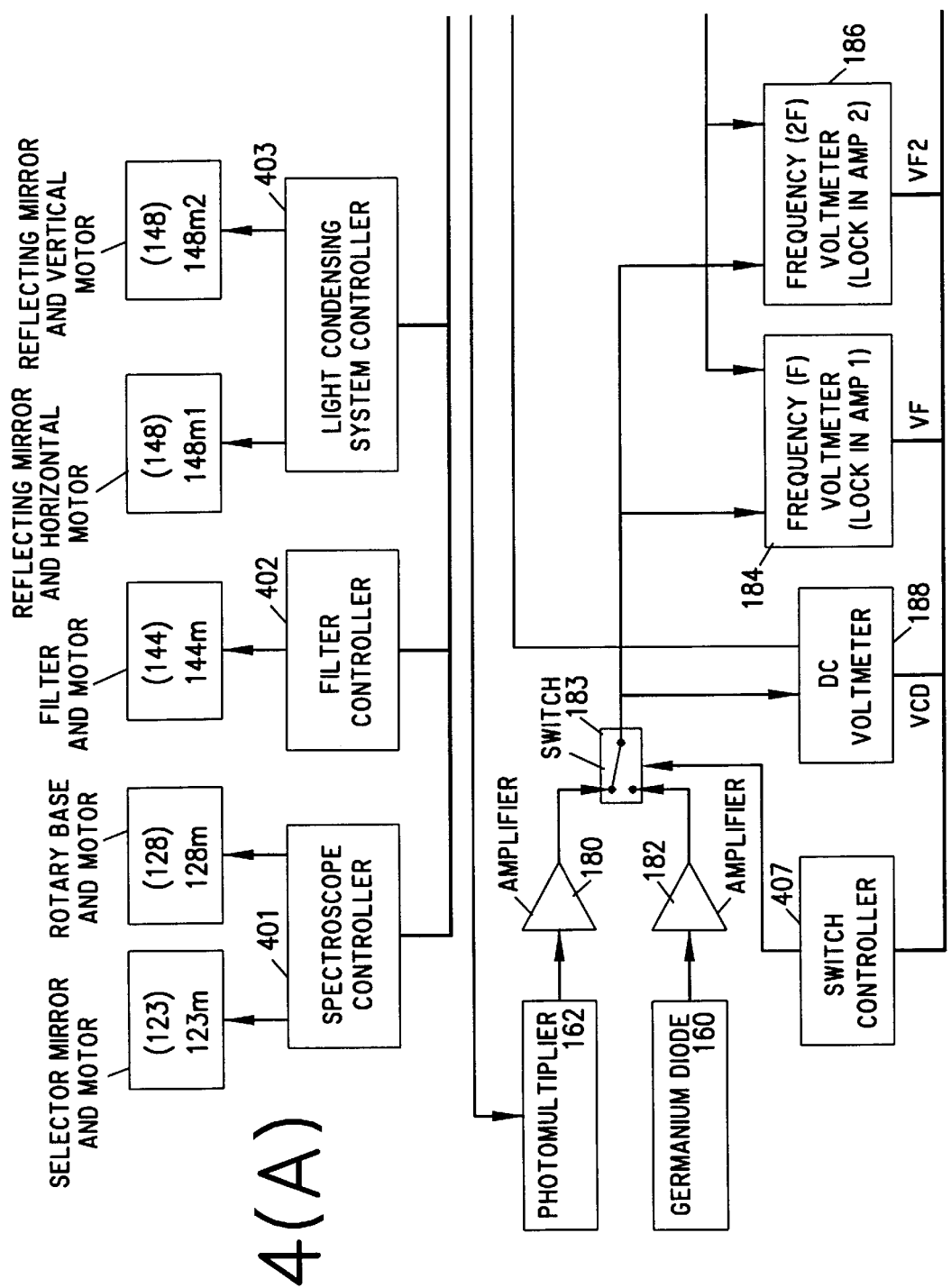
FIG. 4 is a block diagram of an electric system in the measurement apparatus according to the embodiment of the present invention.
Figures 4, 4B:
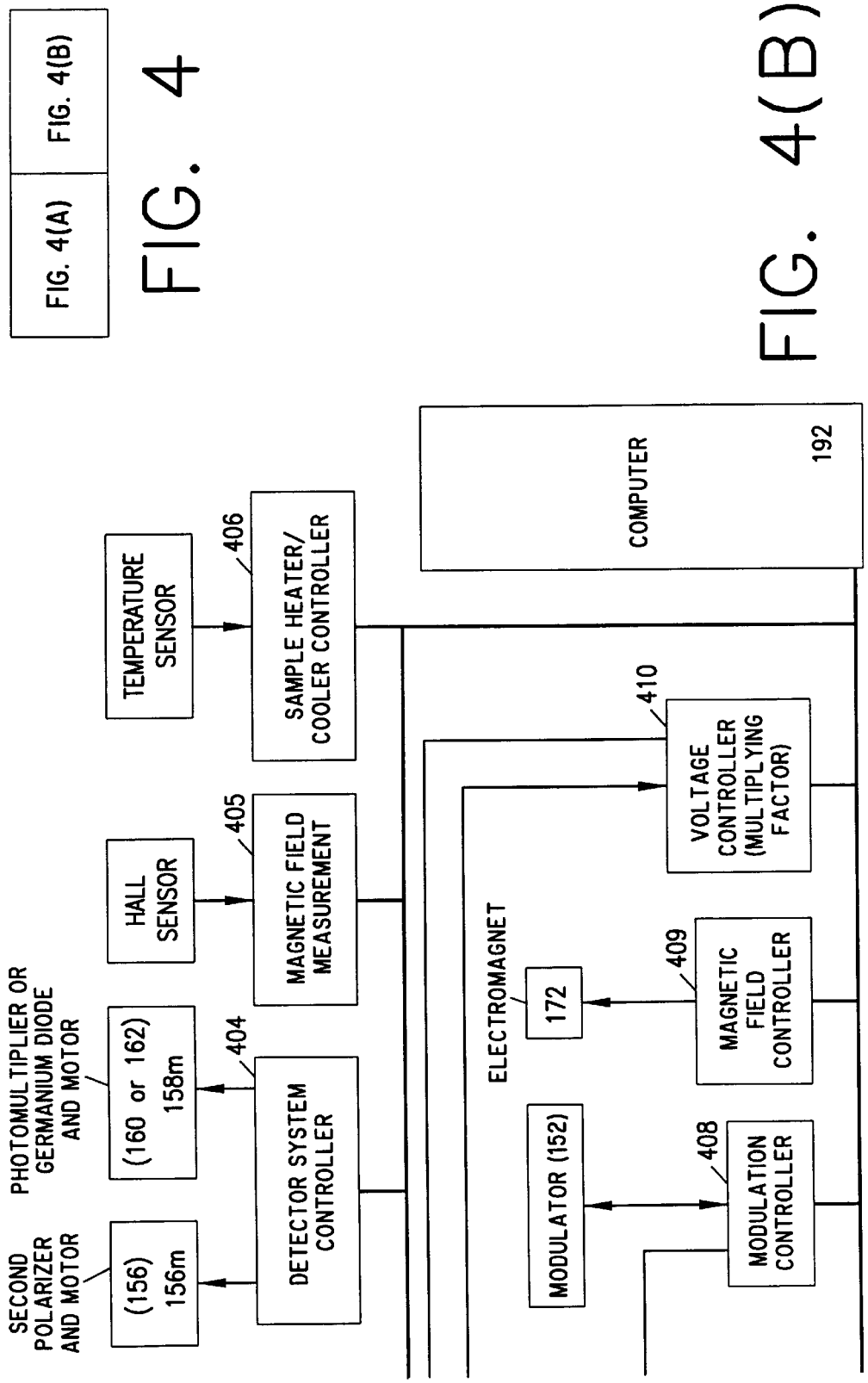

FIG. 4 shows a block diagram of an electrical system mainly composed of the computer 192. The computer 192 controls the selector mirror 123, selects one diffracting grating from the three gratings 130, 132 and 134 and adjusts the angle of the selected grating through a spectroscope controller 401. Similarly, selection is made among the through hole 144a, the filter plates 144b to 144f through a filter controller 402. By controlling the horizontal motor 148m1 and the perpendicular motor 148m2 through a controller 403 for the light condensing system, the light is irradiated on the sample 176. A controller 404 for the detector system rotates the angles of the second polarizer (analyzer) 156 and the concave reflecting mirror 158. A Hall sensor is placed near the sample holder 174, and the magnitude and direction of the magnetic field applied on the sample is inputted to the computer 192. Furthermore, the computer 192 controls the heater and cooler unit. The unit is feedback controlled based on the temperature of the sample 176 detected by the temperature sensor so as the temperature of the sample is kept at a certain value designated by an operator.

The computer 192 also operates the switch 183 by means of a switch controller 407 and inputs the signal from either the amplifier 180 or 182 into the direct current component voltmeter 188, the first lock-in amplifier 184 and the second lock-in amplifier 186. The output of the direct current component voltmeter 188 is inputted in a voltage controller 410. A voltage applied to the photo-multiplier 162 is feedback controlled based on the value detected by the direct current component voltmeter 188 so that the light intensity detected by the direct current component voltmeter 188 is kept substantially at a constant level. The computer 192, via the magnetic field controller 409, regulates electric current to be applied to the electromagnet 172, and, through a modulation controller 408, controls the photo-elastic modulator 152.

Figure 5:
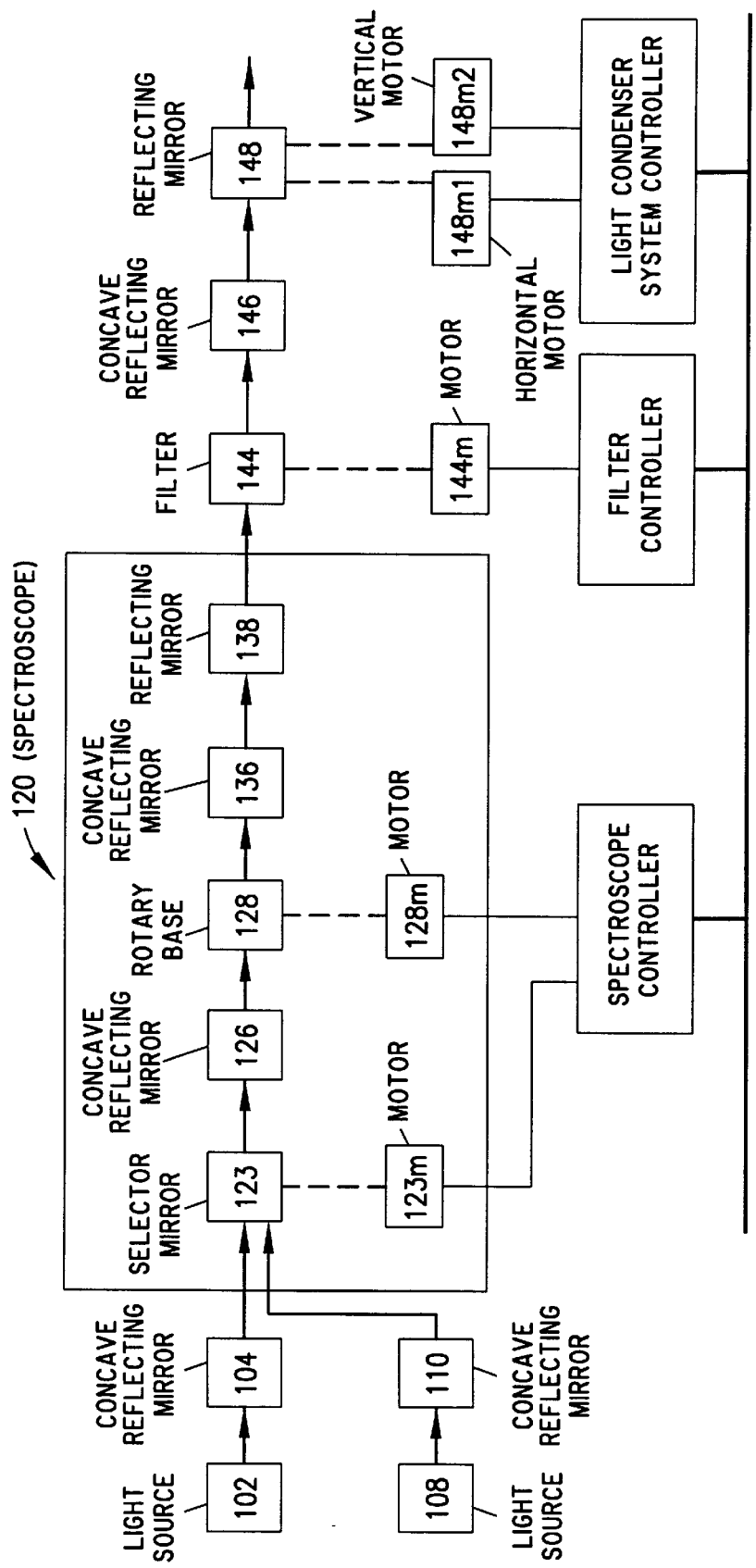
FIG. 5 is a block diagram of irradiation system.

FIG. 5 is a block diagram of the light irradiation system. The arrow indicates the direction of light, the broken line indicates the relation between the motors and the optical components driven thereby, the thin solid line indicates the flow of electric signal, and the thick solid line indicates the control bus of the computer.

Figure 6:
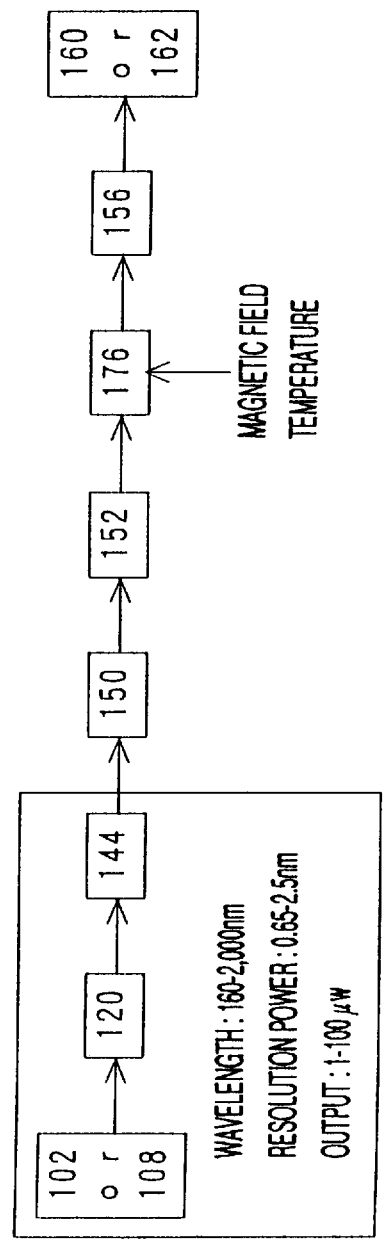
FIG. 6 is a block diagram of the optical path in the measuring apparatus.

FIG. 6 illustrates a block diagram of the light pass from the light source 102 or 108 to the detector 160 or 162.

Figure 7:
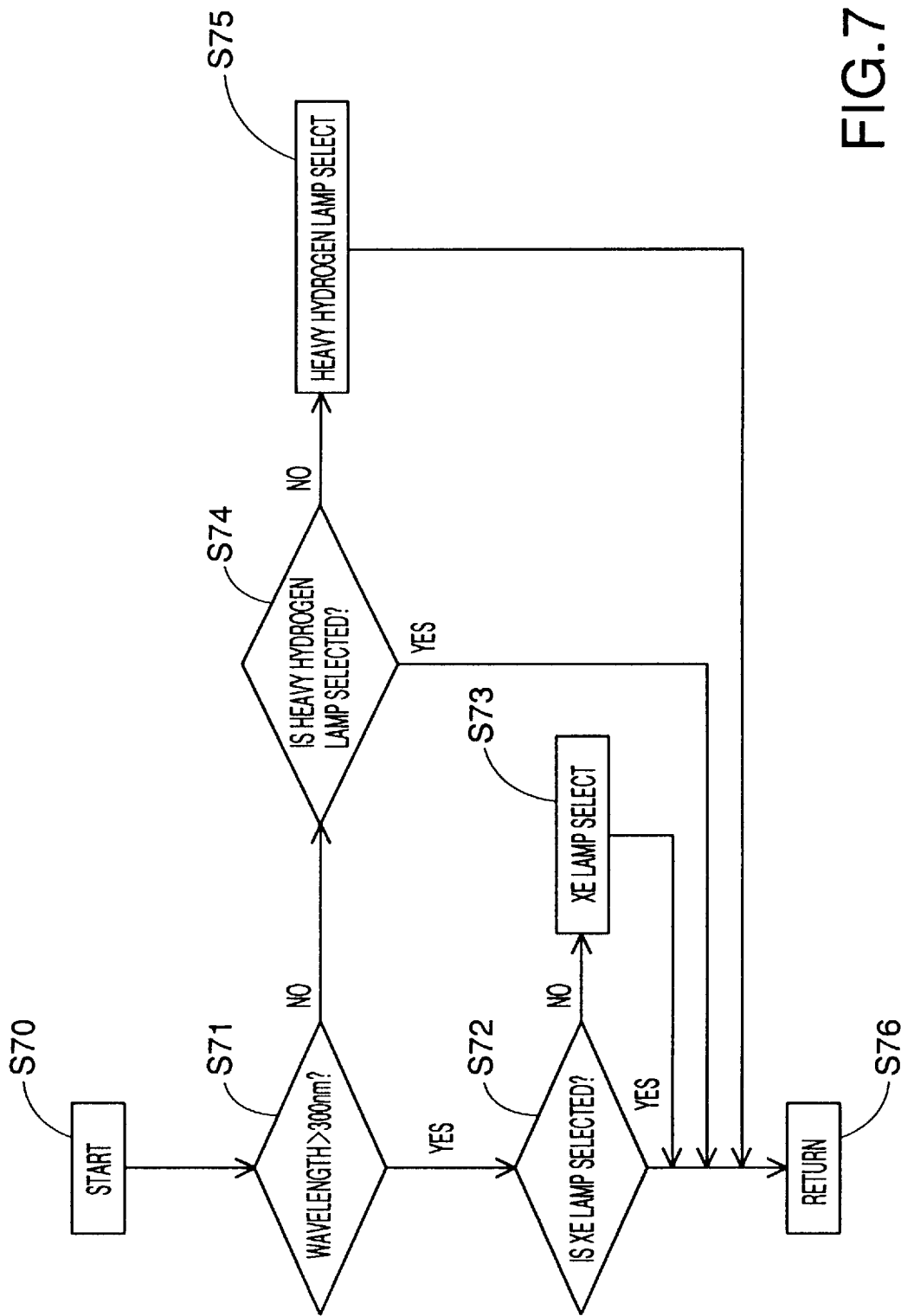
FIG. 7 is a flow chart of lamp selection procedure.

Measurement procedures are shown in FIG. 7 seq. FIG. 7 shows the procedure for selection of a lamp according to the wavelength to be used for measurement. Selection is made on the basis of whether the wavelength is longer or not longer than 300 nm. To be specific, the motor 123m actuates the selector mirror 123 to select the light source from which light is led into the spectroscope 120. The heavy hydrogen lamp 102 is selected for light with wavelength shorter than 300 nm (S74 and S75), and the xenon lamp 108 is selected for wavelength longer than 300 nm (S72 and S73).

Figure 8:
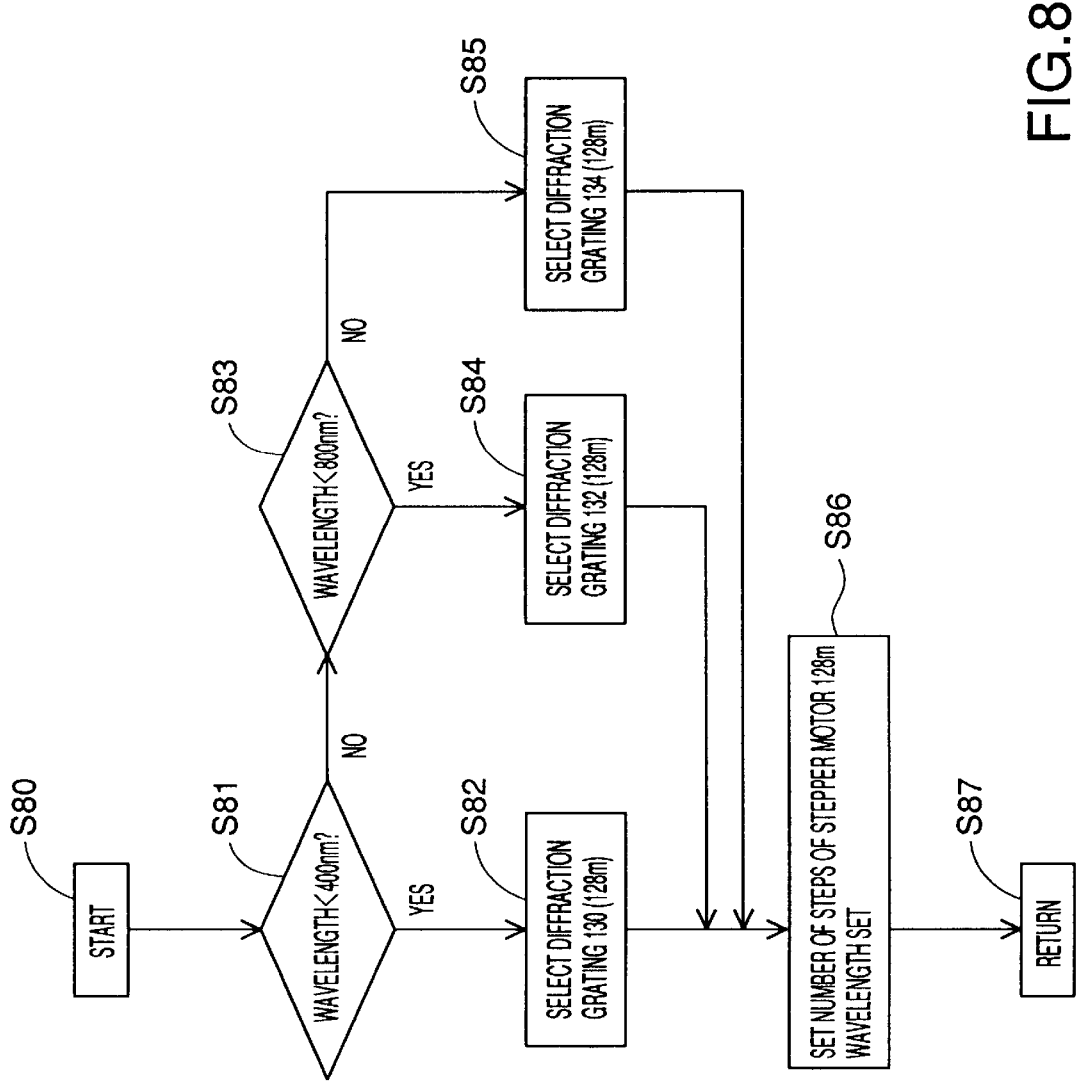
FIG. 8 is a flow chart of procedure for selection of diffraction gratings and adjustment of angle.

FIG. 8 is a flow chart of the procedure for selection of a diffraction grating from the diffraction gratings 130, 132 and 134 and for adjustment of the rotational angle of the selected diffraction grating. For the measurement with the wavelength shorter than 400 nm, the diffraction grating 130 is selected (S82). For the measurement with the wavelength between 400 and 800 nm, the diffraction grating 132 is selected (S84). For the measurement with wavelength longer than 800 nm, the diffraction grating 134 is selected (S85). The reference sign S86 in the figure shows a step of fine tuning the rotational angle of the selected diffraction grating, which decides the wavelength to be used for measurement.

Figure 9:
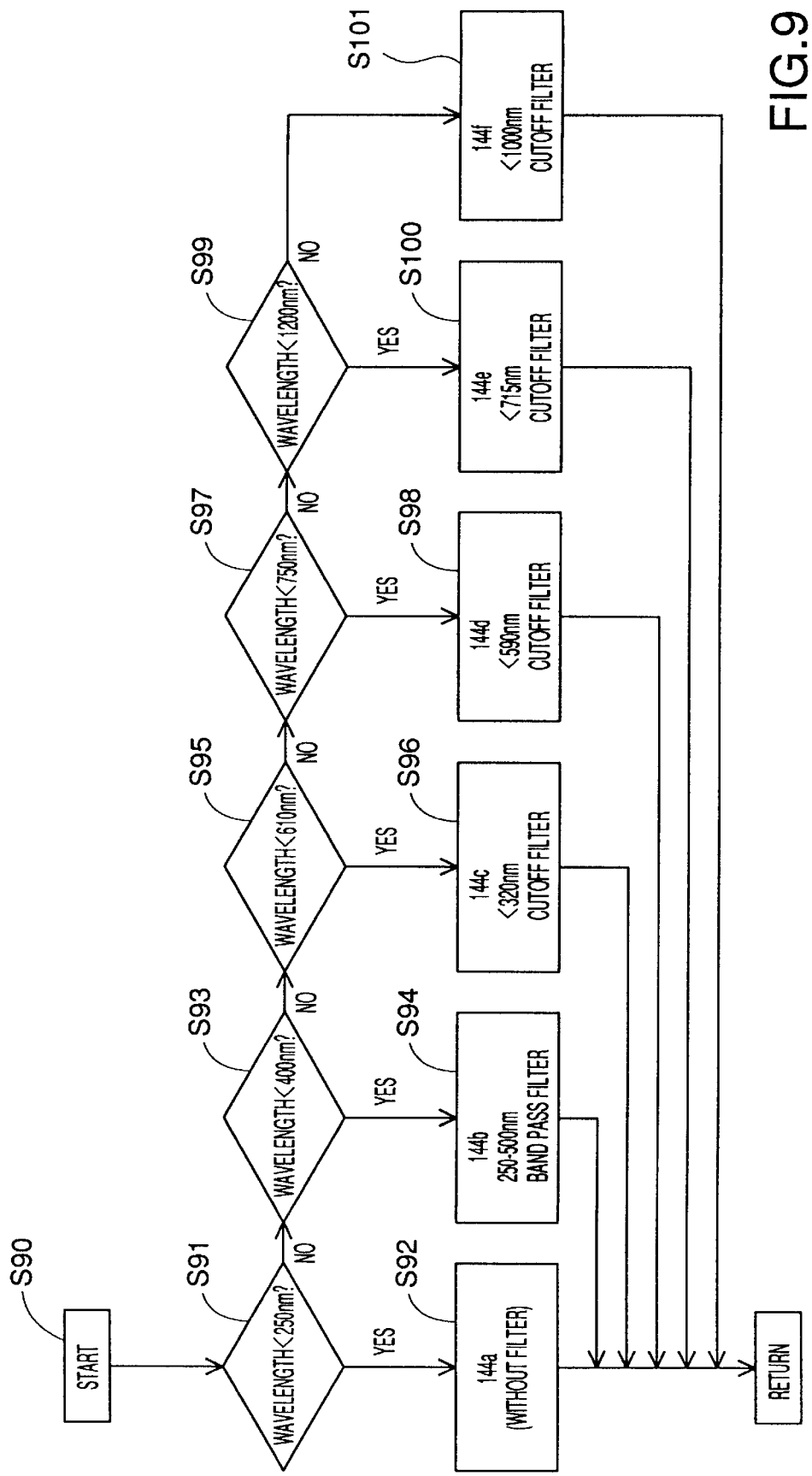
FIG. 9 is a flow chart of procedure for filter selection.

Illustrated in FIG. 9 shows the procedure for the selection of the filter 144. For wavelength not longer than 250 nm, the through hole 144a is selected (S92). When the spectroscope 120 is used to select the wavelength shorter than 250 nm, secondary or higher-order diffraction light that may be irradiated on the sample is shorter than 125 nm in wavelength. The intensity of the light with wavelengths shorter than 125 nm are so weak that they do not have to be filtered out even when the heavy hydrogen lamp is used. For measurement with wavelength between 250 and 400 nm, a band-pass filter 144b which passes light with wavelengths between 250 and 500 nm only is used to eliminate diffraction light of higher order (S93). When measurement is performed with wavelength between 400 and 610 nm, the filter 144c that cuts out light with wavelengths shorter than 320 nm is used to remove diffraction light of higher order (S96). For the measurement with wavelength between 610 and 750 nm, the filter 144d that cuts out light with wavelengths shorter than 590 nm is used to remove diffraction light of higher order (S98). For the measurement with wavelength between 750 and 1200 nm, the filter 144e that cuts out light with wavelengths shorter than 715 nm is used to remove diffraction light of higher order (S100). For the measurement with wavelength longer than 1200 nm, the filter 144f that cuts out light with wavelengths shorter than 1000 nm is used to remove diffraction light of higher order (S101).

Figure 10:
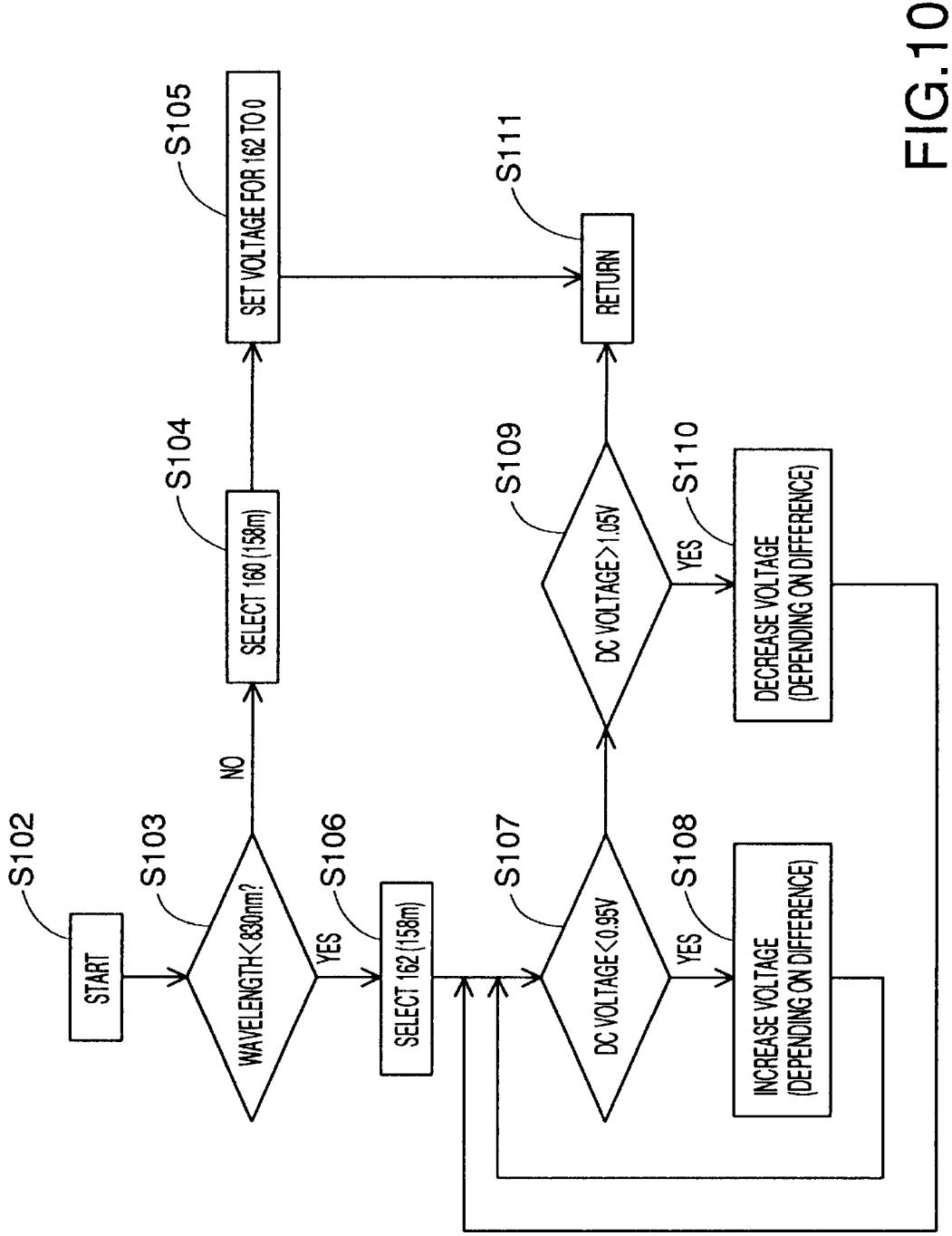
FIG. 10 is a flow chart of procedure for detector selection.

Illustrated in FIG. 10 is a procedure for selecting the detector. For measurement with light with wavelength not longer than 830 nm, the photo-multiplier 162 is selected (S106). In this step of S106, the reflecting mirror 158 is aligned by the motor 158m, and the switch 183 is selected to the photo-multiplier 162. When the photo-multiplier 162 is used, the output of the direct current component voltmeter 188 is monitored (S107, S109). If the voltage is too low (S107), the voltage applied to the photo-multiplier 162 is increased to raise the gain (S108). If the voltage is too high (S109), the voltage is lowered to reduce the gain (S110). In this operation, the quantity of increase or decrease in voltage is feedback controlled by proportioning it to the difference from the reference voltage. Also, hysteresis loop is put in between the step of increasing voltage and the step of decreasing voltage, so as to prevent repetition of overshoot of feedback control.

When measurement is taken with wavelengths longer than 830 nm, the germanium diode 160 is selected (S104; in this case the mirror 158 and the switch 183 are also properly positioned). When the germanium diode 160 is selected, the voltage applied to the photo-multiplier 162 is made zero (S105).

Figure 11:
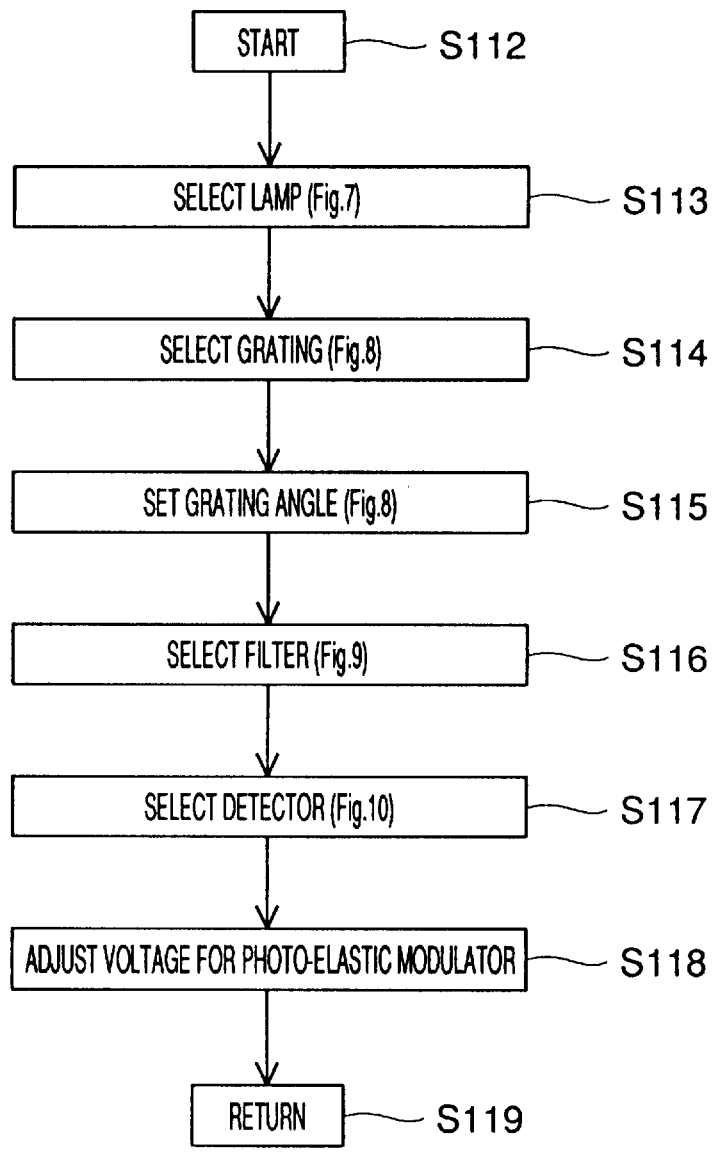
FIG. 11 is a flow chart of overall procedure for measurement preparation.

FIG. 11 is a flow chart of the overall procedure for preparation of measurement. Steps of S113 to S117 have been described in detail in FIGS. 7 to 10. Step S118 shows a procedure for adjusting voltage applied to the photo-elastic modulator 152 in accordance with the wavelength for measurement. This process will be explained in an sample with measuring wavelengths 300 and 600 nm, respectively. When the wavelength of 300 nm is modulated by $\pi/2$ by applying a certain voltage to the photo-elastic modulator 152, the wavelength of 600 nm is not modulated by $\pi/2$ by applying the same voltage. In order to modulate the wavelength of 600 nm by $\pi/2$, higher voltage is required to modulate more strongly and to shift the phase of the light for longer distance. In Step S118, the voltage to be applied to the photo-elastic modulator 152 is adjusted in accordance with the wavelength to be used for measurement. Small voltage is applied when the wavelength is short, and large voltage is applied when the wavelength is long in order to keep the phase shift by modulation substantially constant, irrespective of the wavelength. In the present embodiment, adjustment is so made that the phase shift is slightly smaller than π without being dependent on the wavelength. This phase shift is one where the rotation angle (to be exact, the magneto-optical effect rotation angle) and ellipticity are measured simultaneously with precision.

Figure 12:
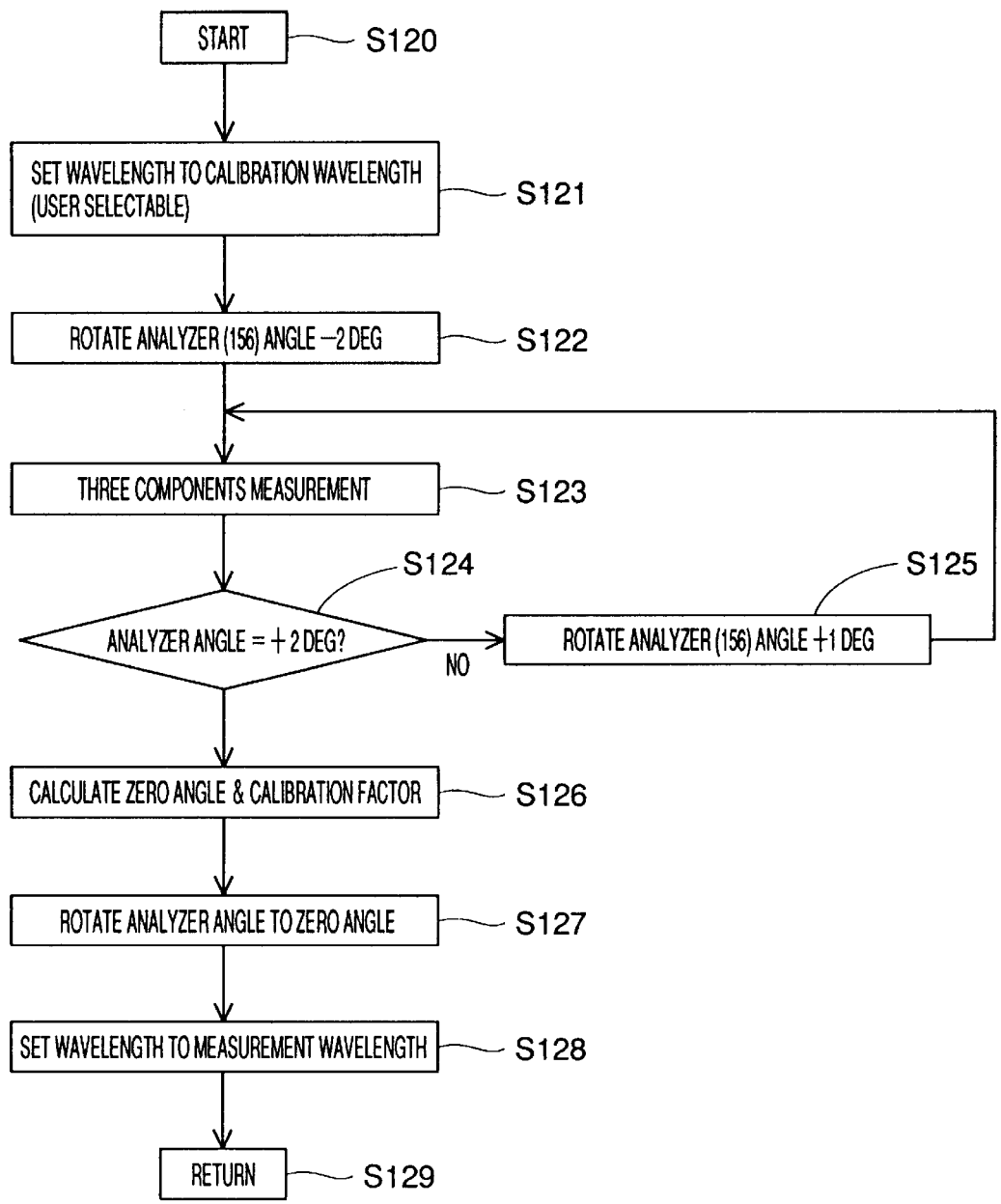
FIG. 12 is a flow chart of calibration procedure.
Figure 13:
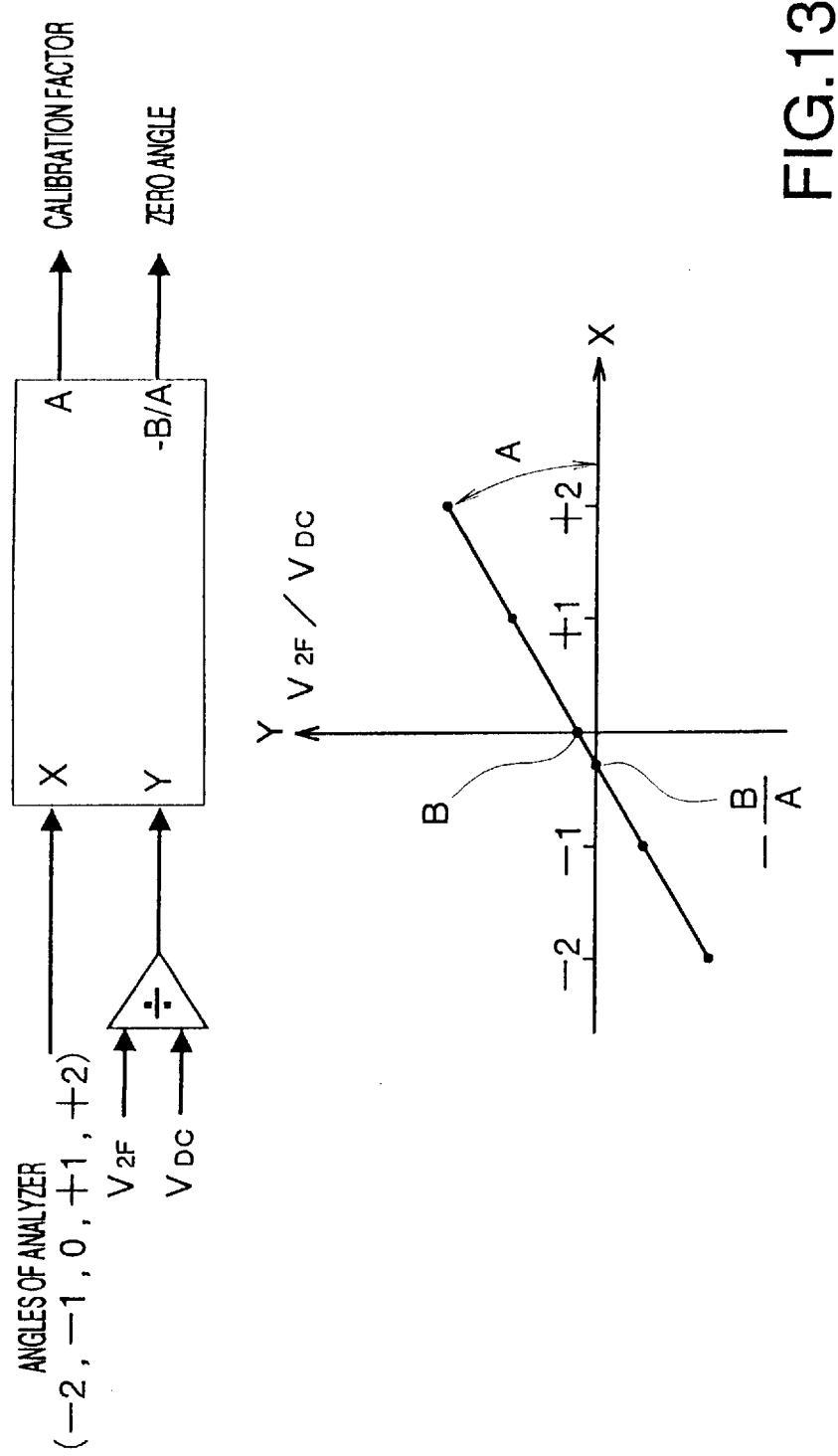
FIG. 13 is a diagram showing details of calibration.

FIGS. 12 and 13 show a procedure for calibration of the apparatus. It is confirmed that the factor for calibration has no dependence on wavelength. The operator himself can choose a wavelength for calibration (S121). However, calibration with wavelength equal to that of the measuring light would be more reliable.

In calibration, the second polarizer 156 (also called analyzer) is first rotated to minus 2 degrees (S122) from the zero degree on the apparatus side to detect the direct current component VDC, the modulation frequency component VF and the frequency component twice as high V2F. After that, the analyzer 156 is rotated +1 by +1 degree (S125) and the same step is repeated. This procedure is continued until +2 degrees (S124). As a result, five measurements are taken. As schematically shown in FIG. 13, the computer analyzes the relationship between the angles X (−2, −1, 0, +1, +2) of the analyzer 156 and V2F/VDC (that is a value obtained from dividing the frequency component twice as high by the direct current component and expressed in Y). To schematically diagram this analysis, a regression line is drawn by a method of least squares on an X-Y coordinates. From the slant of the regression line, the calibration factor A is obtained, and from the value of X where Y=O, the angle of zero is given. This processing is done by the computer 192 (Step S126 in FIG. 12). After this operation, the analyzer 156 is rotated to the angle of zero (S127). Thereafter, the wavelength is set to a measuring wavelength (S128) in preparation for actual measurement. The zero degree on the apparatus side in FIG. 12 is the one intended in the design process that should admit the black wave and block the white wave. The zero degree found in Step S126 is the one actually calibrated.

Figure 14:
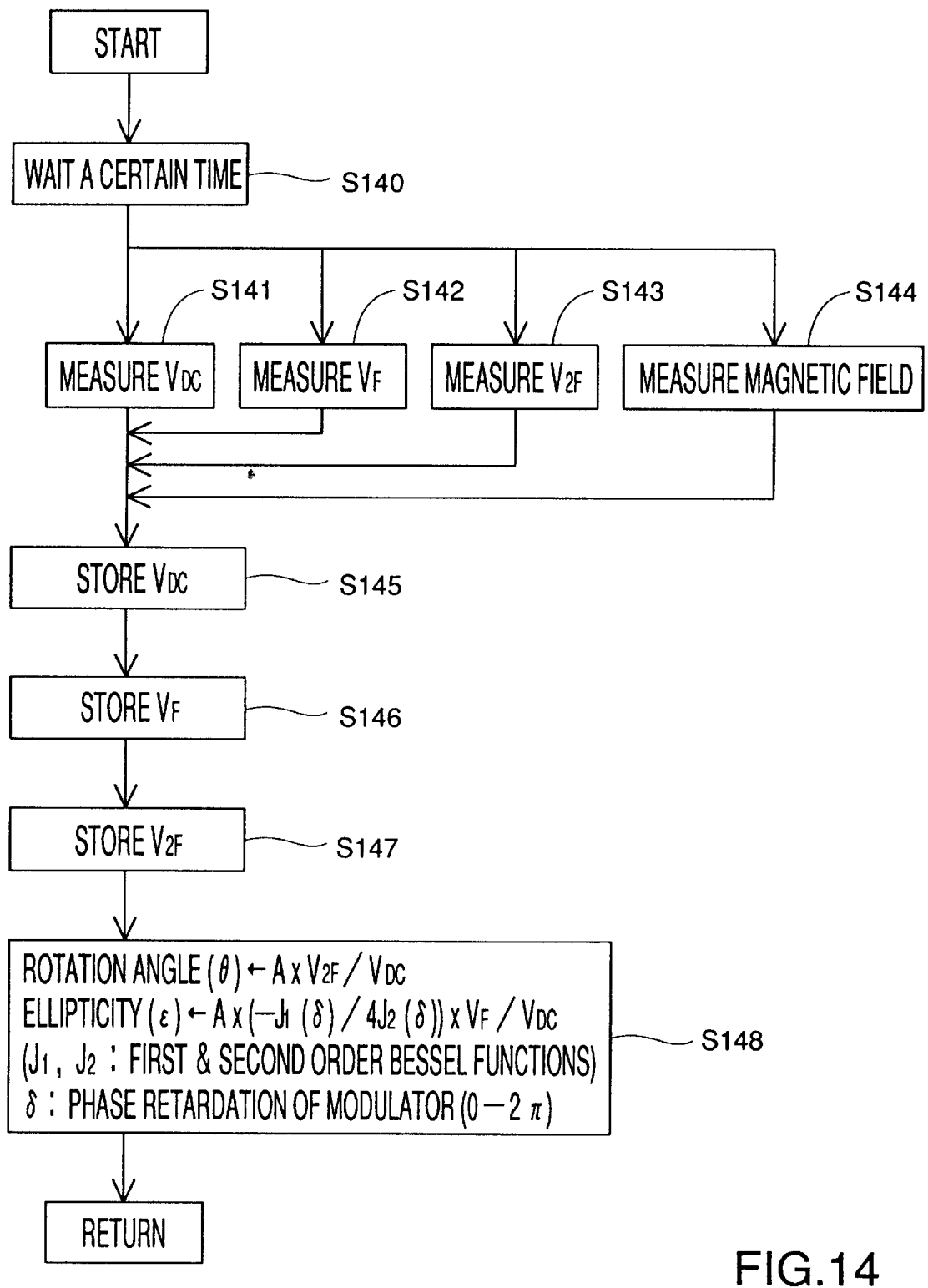
FIG. 14 is a flow chart of measurement procedure in practice.

FIG. 14 shows one sample of actual measurement procedure. In this case, measurements are taken of the direct current component VDC, the modulated frequency component VF and frequency component twice as high V2F and the magnetic field (S141 to S144) after the warm-up time of the amplifier etc. and the measured values are stored in the computer 192 (S145 to S147), from which the rotation angle (θ; magneto-optical Faraday or Kerr rotation angle) and ellipticity (ε) are worked out. The equations for calculation is shown in the Step S148 in FIG. 14, where J1 and J2 indicate the first and second order Bessel functions, respectively, and δ is the phase shift by the photo-elastic modulator. As described, δ is adjusted to 0.383×2π radian (slightly smaller than π) irrespective of the measuring wavelength.

Figure 15:
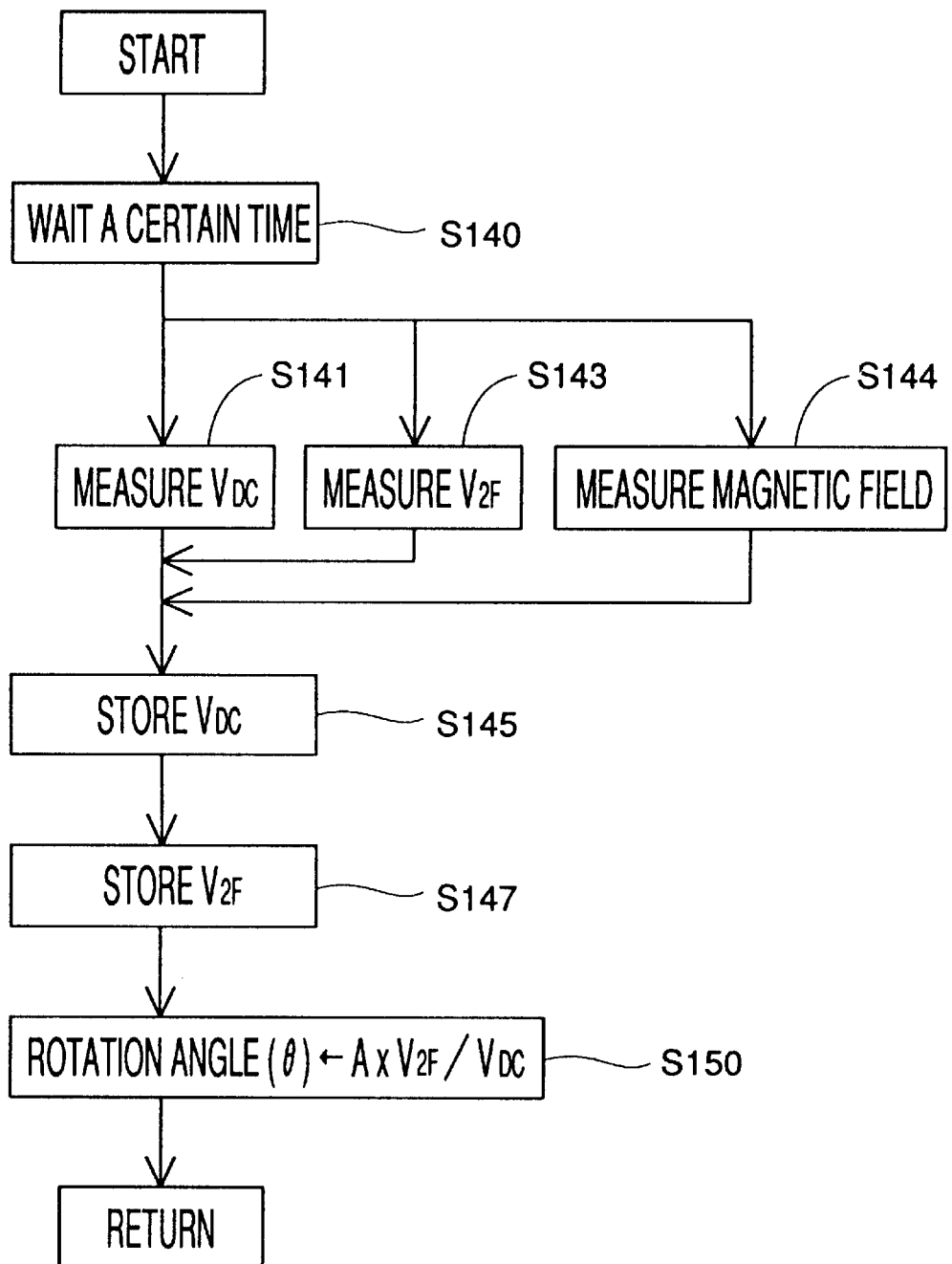
FIG. 15 is a flow chart of procedure for measurement of angle of rotation of magneto-optical effect.
Figure 16:
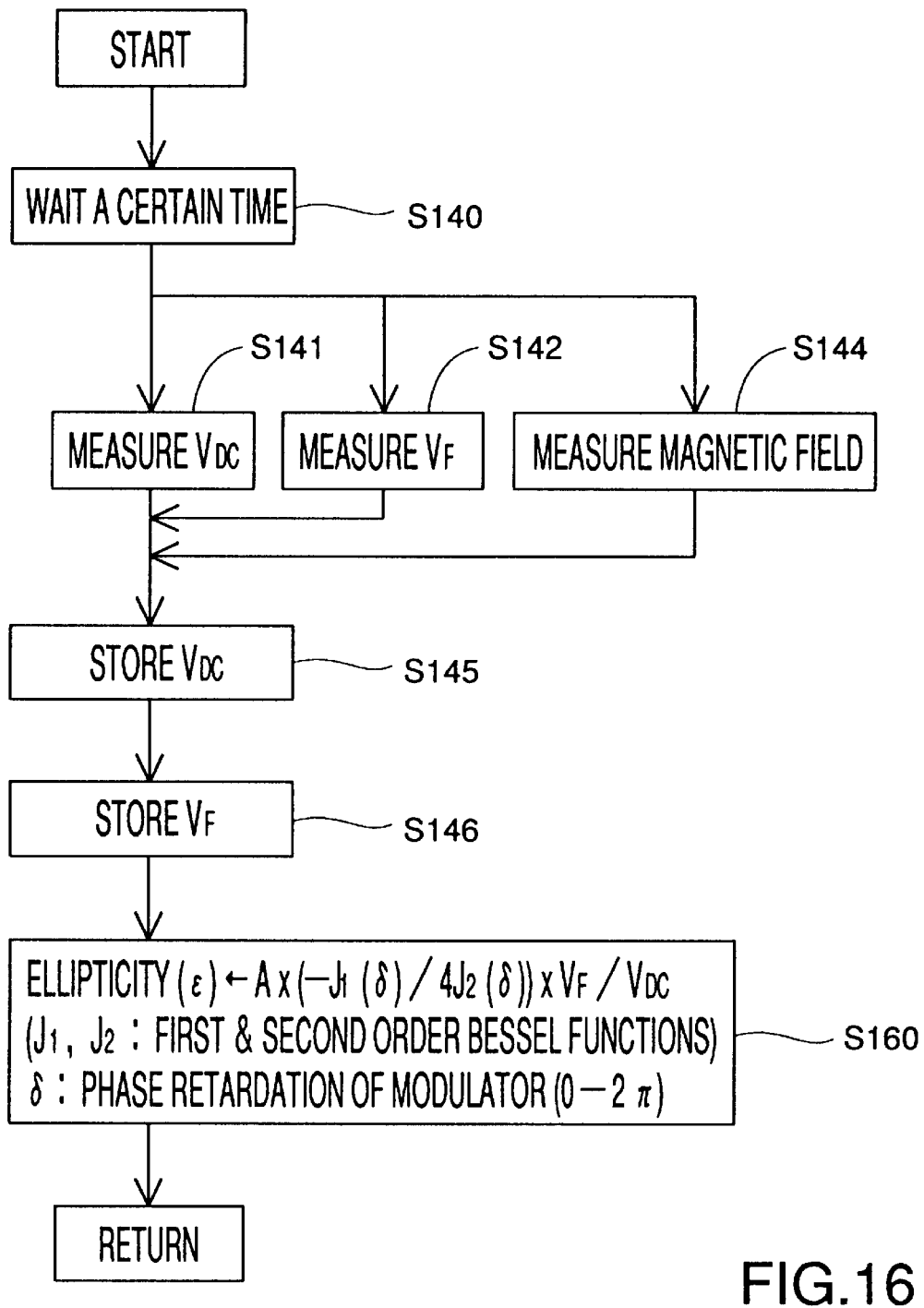
FIG. 16 is a flow chart of procedure for measurement of ellipticity.

FIG. 15 shows a procedure for measurement of the angle of rotation (θ), while FIG. 16 is a flow chart on the determination of ellipticity (ε).

Figure 17:
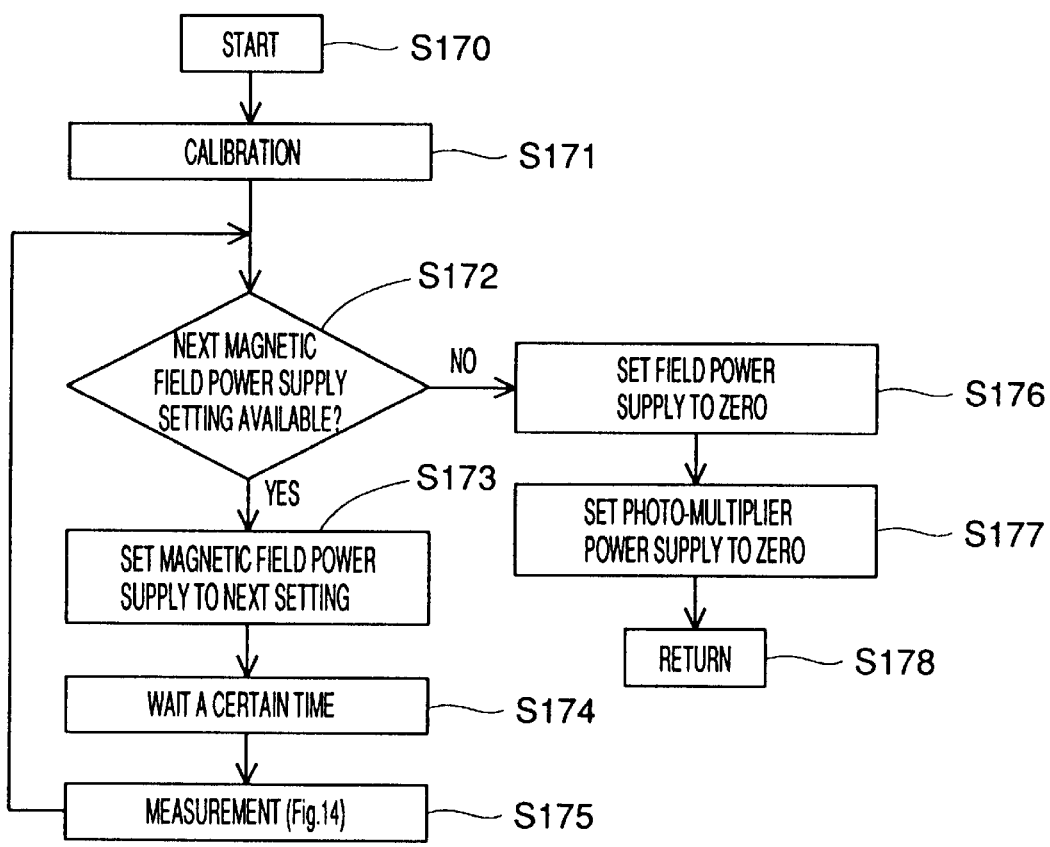
FIG. 17 is a flow chart of procedure for measurement of hysteresis loop.

FIG. 17 is a procedure for measurement of the hysteresis loop with the magnetic field vertically applied to the sample plane by making measurements while changing the magnetic field in the following order: "zero, plus maximum, zero, minus maximum, zero." The magnetic field is predetermined in direction and intensity in relation to the number of measurements so that the changing pattern of magnetic field is obtained during measurements. Before the measurement is started, calibration procedure in FIGS. 12 and 13 is carried (S171). Then, the magnetic field is changed in the predetermined order (S173). When one round of measurements is over, the judgment of the Step S172 is "NO", then the magnetic field is brought to zero (S176) and the voltage applied to the photo-multiplier is set to zero (S177). During measurements, the procedure (S175) is continued with the magnetic field being changed sequentially (S173).

Figure 18:
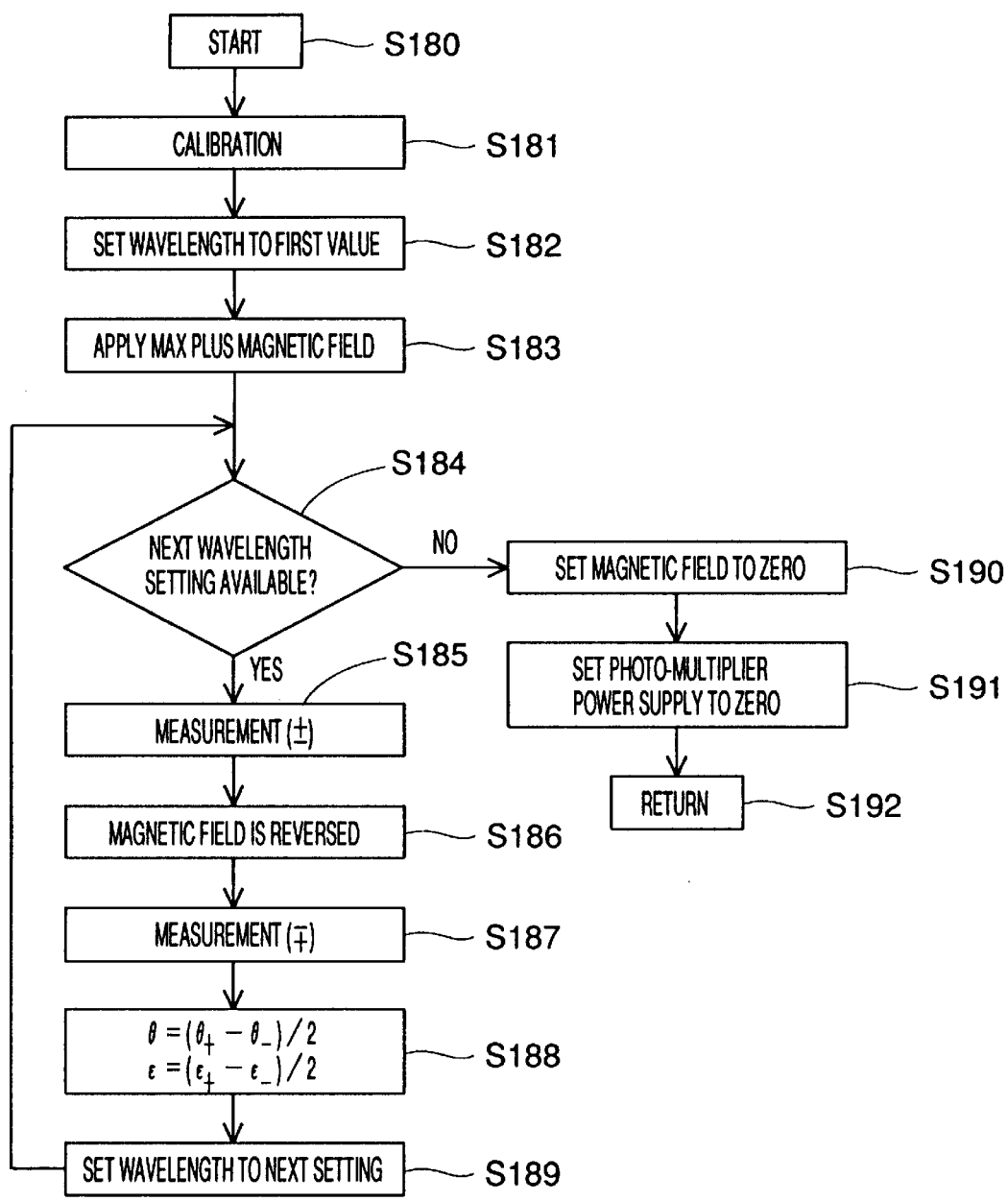
FIG. 18 is a flow chart of procedure for measurement of wavelength dependence (1)

FIG. 18 shows a procedure for measurement of wavelength dependency. This procedure is for measuring the magneto-optical effect when the sample is saturated with the magnetic field. To this end, the maximum plus magnetic field and the maximum minus magnetic field are applied to the sample, and the saturation characteristics are found from the difference of the two measurements. In Step S181, calibration is performed. In Step S182, the wavelength for measurement is set to a first value. In that state, the maximum plus magnetic field is applied (S183). With different wavelengths, a series of measurements are repeated, and when measurement is made with the final wavelength, Step S184 turns No. Then, the measurement procedure ends (S190, S192). During the measurement procedure, measurements are repeated with the maximum plus magnetic field (S185), and then the magnetic field is reversed, and the maximum minus magnetic field is applied (S186), followed by measurement (S187). The difference of measurements of the two different modes is divided by 2 (S188) to work out the rotation angle θ and the ellipticity ε. With different wavelengths, the measurement procedure is repeated (S189).

In measurement with the next wavelength, the minus magnetic field is first applyed and measurement is taken, then the magnetic field is reversed to plus for measurement (S185, S186, S187). As shown, the different magnetic field modes are applied on each wavelength, on the first wavelength plus then minus, on the second wavelength minus then plus. In this way, the order of applying magnetic fields is also reversed alternately. Measurement with the whole range of wavelengths reveals the dependency on wavelength.

Figure 19:
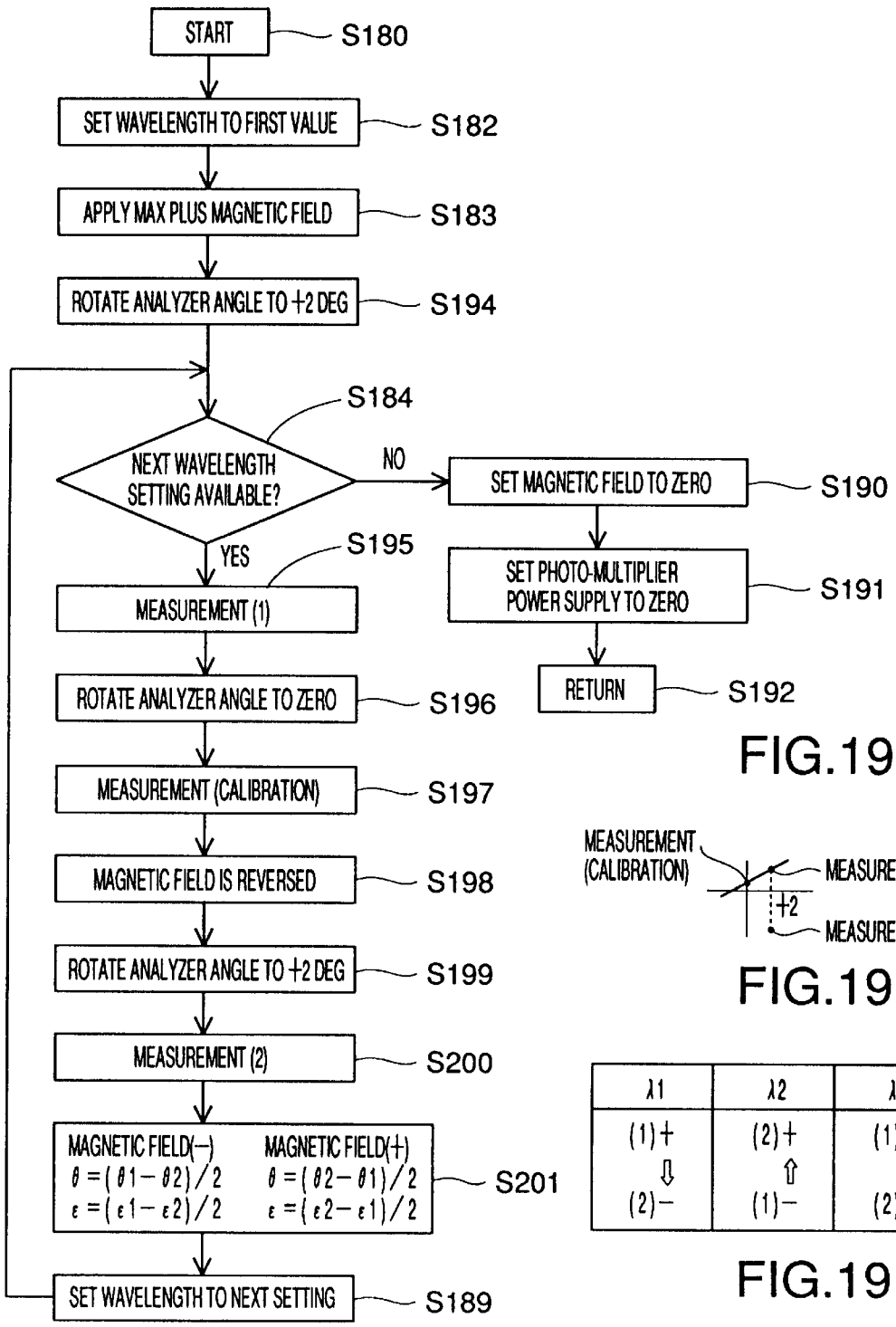
FIG. 19(A) is a flow chart of procedure for measurement of wavelength dependence (2)
FIGS. 19(B) and 19(C) illustrate calibration principle.

FIG. 19 is an improved procedure for determination of wavelength dependency. In this procedure, calibration is performed with each wavelength. Therefore, measurement is taken with the analyzer, first at +2 degrees (S194, S195), then at O degree (S196, S197). This gives a calibration line as shown in FIG. 19(B). From that, the calibration factor for that wavelength is calculated. In the present embodiment, the magneto-optical effect is measured with the analyzer positioned at +2 degrees (S194 and S195) (S199 and S200). That is, measurement is not done at zero degree. However, the difference between the positive magnetic field and the negative magnetic field is found in Step S201, and the influence by deviation from an angle of zero degree is thus offset, and reliable measurements are obtained.

Figure 20:
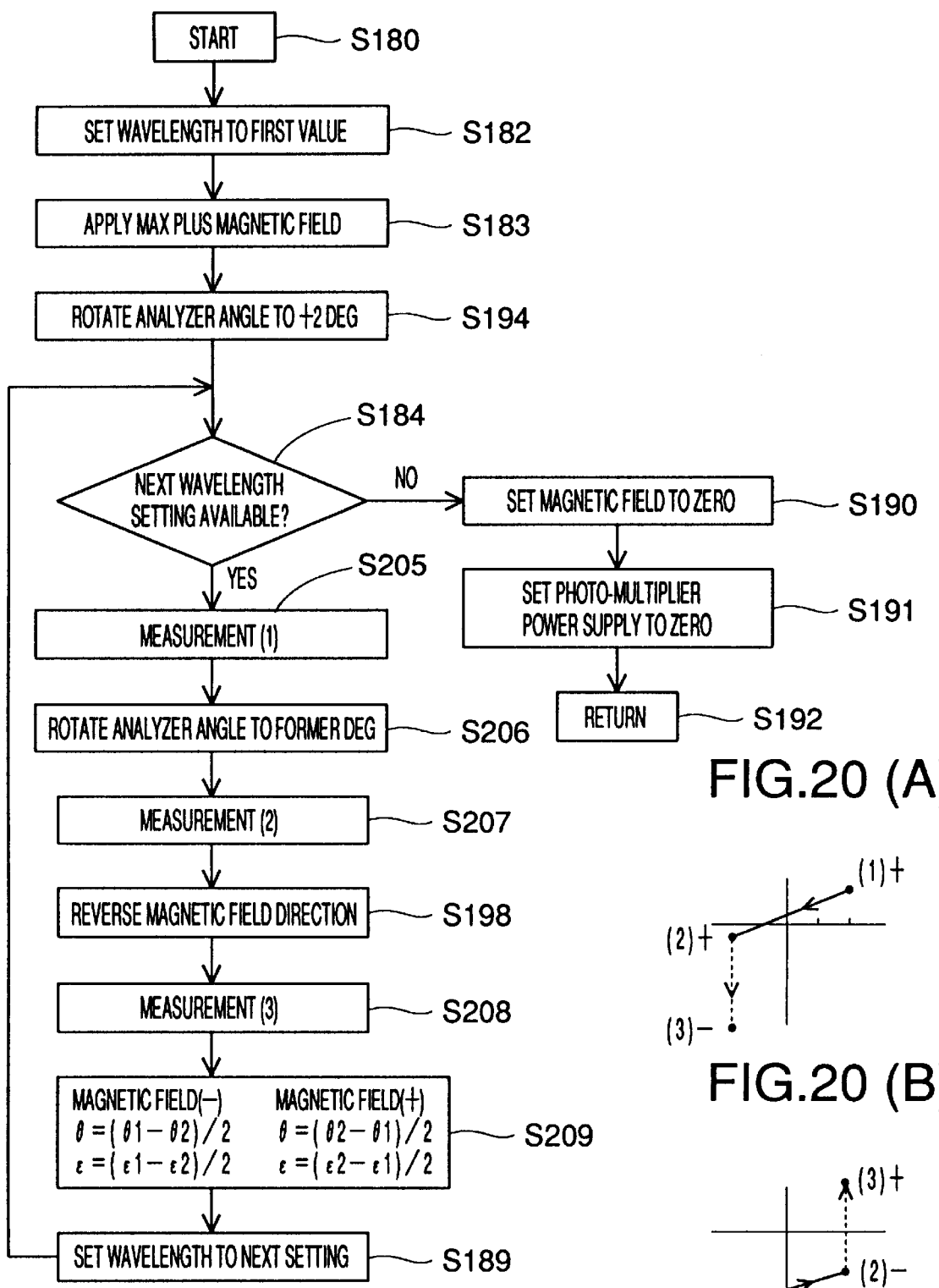
FIG. 20(A) is a flow chart of procedure for measurement of wavelength dependence (3)
FIGS. 20(B) and 20(C) illustrate calibration principle.

FIG. 20 shows another example which is improved the same way as that in FIG. 19 and which uses the analyzer either at +2 degrees or −2 degrees. In this improved example, with a certain wavelength, a plus magnetic field is applied for calibration (FIG. 20(B)), and with the next wavelength, a minus magnetic field is applied (FIG. 20(C)). This reduces the number of magnetic field reversings to a minimum, substantially saving the measurement time.

The embodiment that has been described is one in which the present invention is applied to an apparatus for measurement by modulated waves of circularly polarized light. The present invention can be applied to apparatuses by the crossed-Nicols, Farady cell, rotational analyzer methods.

According to the present invention, a heavy hydrogen lamp is used as a light source, the light path is secured in an oxygen-free gas, and no substantial attenuation of short wavelength light is made by the optical component parts. For these reasons, magneto-optical effect can be measured at wavelengths less than 200 nm, and therefore, the present invention is expected to greatly contribute to the development and progress of ultra-high density memory technology in the future.

While the invention has been described with reference to a preferred embodiment thereof, it is to be understood that modifications or variations may be easily made without departing from the scope of the present invention which is defined by the appended claims.

What is claimed is:

1. An apparatus for measuring magneto-optical effect, comprising:
   a light source including a heavy hydrogen lamp for emitting light;
   a spectroscope for separating light emitted by the light source into a spectral component of a preselected wavelength, wherein the spectroscope does not include any of a lens and a prism;
   a first polarizer for polarizing the separated light spectrum taken out by the spectroscope and transmitting the light from the first polarizer to irradiate a sample;
   means for applying a magnetic field to the sample;
   a second polarizer for receiving light from the first polarizer which is one of transmitted through and reflected by the sample;
   a photo-detector for detecting an intensity of light transmitted by the second polarizer
   wherein a light path from the light source to the photo-detector is housed in a container
   having an oxygen free atmosphere therein.

2. The apparatus as defined in claim 1, further comprising:
   means for modulating, at a specific frequency, light irradiated on the sample; and
   means for obtaining from a value corresponding to the intensity detected by said detector the intensities of a direct current component, modulation frequency component and frequency component twice as high,
   whereby simultaneous measurements of rotation angle and ellipticity of the magneto-optical effect is permitted.

3. The apparatus as defined in claim 1, wherein said light source further includes a second lamp for emitting light with a wavelength range of longer than those of the heavy hydrogen lamp, and wherein said spectroscope is capable of selecting the lamp from which the light comes so that measurements over a wide wavelength range is permitted.

4. The apparatus as defined in claim 1, wherein a light condensing system is made up of reflecting mirrors without containing lenses.

5. The apparatus as defined in claim 1, further comprising a concave reflecting mirror positioned to reflect the light from the light source to the spectroscope, the concave reflecting mirror comprising polished quartz coated with platinum.

6. The apparatus as defined in claim 5, wherein the concave mirror further comprises a top coating of Al—$MgF_2$.

7. The apparatus as defined in claim 1, further comprising a sample holder including means for heating and cooling the sample.

8. The apparatus as defined in claim 1, wherein the spectroscope comprises three diffraction gratings.

9. The apparatus as defined in claim 8, further comprising a rotary base on which the spectroscope is mounted, wherein the pre-selected wavelengths are chosen by rotating the rotary base.

10. An apparatus contained within a substantially oxygen-free environment for measuring magneto-optical effects, the apparatus comprising:
    a light source comprising a heavy hydrogen lamp;
    a spectroscope, wherein the spectroscope transmits a selected portion of the light from the light source, the selected portion of light having pre-selected wavelengths, wherein the spectroscope does not include any of a lens and a prism; and
    a photo-detector for measuring an intensity of light received from a sample irradiated with light from the spectroscope, wherein the light received by the photo-detector is one of light reflected by and light transmitted from the sample.

11. The apparatus as defined in claim 10, further comprising:
    first and second polarizers, the first polarizer being disposed between the spectroscope and the light source and the second polarizer being disposed between the sample and the photo-detector; and
    means for applying a magnetic field to the sample.

12. The apparatus as defined in claim 11, further comprising:
    means for modulating the selected portion of light, wherein the modulation occurs at predetermined frequencies; and
    means for determining, based upon the intensity of the light measured by the photo-detector, an intensity of a direct current component, a modulation frequency component and a second harmonic frequency component.

13. The apparatus as defined in claim 10, further comprising a concave reflecting mirror positioned to reflect the light from the light source to the spectroscope, the concave reflecting mirror comprising polished quartz coated with platinum.

14. The apparatus as defined in claim 13, wherein the concave mirror further comprises a top coating of Al—$MgF_2$.

15. The apparatus as defined in claim 10, further comprising a sample holder including means for heating and cooling the sample.

16. The apparatus as defined in claim 10, wherein the spectroscope comprises three diffraction gratings.

17. The apparatus as defined in claim 16, further comprising a rotary base on which the spectroscope is mounted, wherein the pre-selected wavelengths are chosen by rotating the rotary base.

18. An apparatus contained within a substantially oxygen-free environment for measuring magneto-optical effects, the apparatus comprising:
    means for producing light having wavelengths less than 200 nanometers;
    means for separating the light into spectral components having preselected wavelengths;
    means for polarizing the spectral components of light, and irradiating a sample with the polarized light;
    means for applying a magnetic field to the sample;
    means for polarizing light which is one of light transmitted by and light reflected from the sample; and
    means for detecting an intensity of the light which is one of light transmitted by and light reflected from the sample.

19. The apparatus as defined in claim 18, wherein the means for separating the light into spectral components comprises a spectroscope having three diffraction gratings.

20. The apparatus as defined in claim 19, further comprising means for producing light having wavelengths greater than 200 nanometers to irradiate the sample with wavelengths over a wide frequency range.

* * * * *

UNITED STATES PATENT AND TRADEMARK OFFICE
CERTIFICATE OF CORRECTION

PATENT NO. : 5,822,063
DATED : October 13, 1998
INVENTOR(S) : Takao Suzuki et al.

It is certified that error appears in the above-identified patent and that said Letters Patent is hereby corrected as shown below:

Title page,
Item [73], Assignee, add second assignee, -- Toyota School Foundation, Aichi, Japan --.

Signed and Sealed this

First Day of November, 2005

JON W. DUDAS
*Director of the United States Patent and Trademark Office*